(12) United States Patent
Radjy

(10) Patent No.: US 10,067,115 B2
(45) Date of Patent: Sep. 4, 2018

(54) SYSTEMS, APPARATUS AND METHODS FOR OBTAINING MEASUREMENTS CONCERNING THE STRENGTH AND PERFORMANCE OF CONCRETE MIXTURES

(71) Applicant: QUIPIP, LLC, Pittsburgh, PA (US)

(72) Inventor: Farrokh F. Radjy, Pittsburgh, PA (US)

(73) Assignee: QUIPIP, LLC, Pittsburgh, PA (US)

( * ) Notice: Subject to any disclaimer, the term of this patent is extended or adjusted under 35 U.S.C. 154(b) by 0 days.

(21) Appl. No.: 15/414,401

(22) Filed: Jan. 24, 2017

(65) Prior Publication Data
US 2017/0212094 A1    Jul. 27, 2017

Related U.S. Application Data

(60) Provisional application No. 62/356,354, filed on Jun. 29, 2016, provisional application No. 62/343,587, filed on May 31, 2016, provisional application No. 62/287,072, filed on Jan. 26, 2016.

(51) Int. Cl.
*G01N 33/38* (2006.01)

(52) U.S. Cl.
CPC .................. *G01N 33/383* (2013.01)

(58) Field of Classification Search
CPC .............. G01N 33/383; G01N 33/33; G01N 2021/7766; G01N 2021/7793; G01N 2201/04; G01N 11/00; G01N 25/16; G01N 33/38

See application file for complete search history.

(56) References Cited

U.S. PATENT DOCUMENTS

| | | |
|---|---|---|
| 2002/0031165 A1 | 3/2002 | Zollinger et al. |
| 2011/0094295 A1 | 4/2011 | Meadows et al. |
| 2011/0120576 A1 | 5/2011 | Sigouin et al. |
| 2015/0068523 A1 | 3/2015 | Powers et al. |
| 2015/0212061 A1 | 7/2015 | Radjy |

(Continued)

FOREIGN PATENT DOCUMENTS

CN    205027749 U  *  9/2015

OTHER PUBLICATIONS http://www.stle.org/Images/pdf/LubeCafe/Components/Seals/Typical_Labyrinth_Seals_with_Stepped_LabyrinthFinal.pdf retrieved Dec. 23, 2017 (created Sep. 18, 2015).*

(Continued)

*Primary Examiner* — Paul D Lee
*Assistant Examiner* — Mark Crohn
(74) *Attorney, Agent, or Firm* — Lucas & Mercanti, LLP

(57) ABSTRACT

A smart cap system includes a cap adapted to fit on a concrete test cylinder, the cap including one or more internal surfaces, and one or more sensors disposed in or on the one or more internal surfaces of the cap, the one or more sensors being adapted to obtain a measurement of a characteristic of a concrete mixture disposed in the test cylinder. The cap may be adapted to fit on one of a 4×8-inch cylinder and a 6×12-inch cylinder. The one or more sensors may include one of a temperature sensor, a humidity sensor, a chronometer, a heat flow sensor, a motion sensor, a pH sensor, a location detector, a GPS sensor, an accelerometer, a triangulation sensor, a thermoelectric heat flow sensor, a salinity sensor, a macro fiber composite (MFC) sensor, and a capillary sensor.

6 Claims, 43 Drawing Sheets

(56) References Cited

U.S. PATENT DOCUMENTS

2015/0315078 A1   11/2015   Feldman et al.

OTHER PUBLICATIONS

Jiang et al (CN205027749) Machine Translation obtained from Google on Apr. 19, 2018.*
Jiang et al (CN205027749) Derwent Record.*
International Search Report dated Apr. 10, 2017 from corresponding to International Application No. PCT/US2017/014756.
Written Opinion of the International Searching Authority dated Apr. 10, 2017 from corresponding to International Application No. PCT/US2017/014756.

* cited by examiner

SYSTEMS, APPARATUS AND METHODS FOR OBTAINING MEASUREMENTS CONCERNING THE STRENGTH AND PERFORMANCE OF CONCRETE MIXTURES

This application claims priority from U.S. Provisional Application No. 62/287,072 filed Jan. 26, 2016. This application claims the benefit of U.S. Provisional Application No. 62/343,587 filed May 31, 2016 and U.S. Provisional Application No. 62/356,354 filed Jun. 29, 2016. The contents of each of these applications are incorporated by reference.

TECHNICAL FIELD

This specification relates generally to the construction field, and more particularly to systems, apparatus, and methods for obtaining data concerning the performance of concrete mixtures.

BACKGROUND

Concrete is generally used within the industry to refer to a mixture of cement, sand, stone, and water which upon aging turns into a hardened mass. The term concrete, as used in the specification and claims herein, means not only concrete as it is generally defined in the industry (cement, sand and stone), but it also means mortar (cement, sand and water) and cement (cement and water which hardens into a solid mass upon aging).

In the construction field, after a batch of concrete has been produced for use at a particular site, it is useful to be able to obtain data concerning certain performance characteristics such as the in-place strength of the batch. Accurate prediction of concrete performance can increase the quality of the end product, and can provide other benefits such as allowing the use of accelerated construction schedules.

Several methods for testing and monitoring in-place strength of a concrete mass have been incorporated into the American Standard Testing Methods, including ASTM C805 (The Rebound Number Method—the so-called Swiss Hammer Method), ASTM C597 (The Pulse Velocity (Sonic) Method), and ASTM C900 (The Pullout Strength Method).

In accordance with standards set forth in ASTM C31 (Standard Practice for Making and Curing Concrete Test Specimens in the Field), the compressive strength of concrete is measured to ensure that concrete delivered to a project meets the requirements of the job specification and for quality control. In order to test the compressive strength of concrete, cylindrical test specimens are cast in test cylinders and stored in the field until the concrete hardens.

In accordance with the standards, typically 4×8-inch or 6×12-inch test cylinders are used, and the concrete specimens are stored in a carefully selected location for a predetermined period of time. When making cylinders for acceptance of concrete, the field technician must test properties of the fresh concrete including temperature, slump, density (unit weight) and air content.

There is an ongoing need for improved systems and methods for measuring and predicting the strength and performance of concrete.

SUMMARY

In accordance with an embodiment, a smart cap system includes a cap adapted to fit on a standard concrete test cylinder, the cap comprising one or more internal surfaces, and one or more sensors disposed on the one or more internal surfaces of the cap, the one or more sensors being adapted to obtain measurement data. Additionally, by using a double-walled construction with air insulation or using another insulation method, the cap is insulated (so that its temperature sensor measures the concrete temperature by being closely positioned to the cylinder surface).

In one embodiment, the cap includes a double-walled structure having first and second walls and a volume between the first and second walls, wherein the volume holds one of air and a selected insulating material.

In another embodiment, the one or more sensors are adapted to obtain a measurement of a characteristic of a concrete mixture disposed in the test cylinder.

In another embodiment, the cap is adapted to fit on one of a 4×8-inch cylinder, a 6×12-inch cylinder, a 150 mm cube, or a 200 mm cube.

In another embodiment, the one or more sensors comprise one of a temperature sensor, a humidity sensor, a pH sensor, a chronometer, a heat flow sensor, a motion sensor, a location detector, a GPS sensor, a MFC sensor, and a capillary sensor.

In another embodiment, a smart cap system includes a memory adapted to store data, and a processor adapted to receive from the one or more sensors measurement data relating to the measurement of the characteristic of the concrete mixture, and generate a prediction of a second characteristic of the concrete mixture based on the measurement data.

In one embodiment, the one or more sensors include a capillary sensor system, wherein the capillary sensor system includes a tube and a temperature sensor.

In another embodiment, the one or more surfaces of the cap include a material, wherein the one or more sensors are embedded in the material.

In accordance with another embodiment, a smart cap system includes a sensor holder system disposed on one of the one or more internal surfaces of the cap. The sensor holder system includes a sensor enclosure component adapted to hold the one or more sensors. The sensor enclosure component includes a slot or volume adapted to hold the one or more sensors, and a surface comprising one or more holes adapted to allow a flow of air to pass into the volume. The sensor holder system also includes a cover component adapted to cover and protect the sensor enclosure component, and a fabric membrane disposed between the sensor enclosure component and the cover component.

In accordance with another embodiment, a method is provided. A cap is placed onto a cylinder that contains concrete, the cap comprising a sensor adapted to measure a first characteristic of the concrete. Measurement data relating to a measurement of the first characteristic is received from the sensor, while the concrete is setting. A prediction of a second characteristic of the concrete is generated, based on the measurement data.

In accordance with another embodiment, a system includes a first sensing device adapted to obtain a first measurement of a temperature and a second measurement of humidity of a quantity of concrete in a structure, the quantity of concrete being associated with a particular batch of concrete. The system also includes a second sensing device adapted to obtain a third measurement of temperature and a fourth measurement of humidity of a specimen of concrete in a test cylinder, the specimen of concrete being associated with the particular batch. The system further includes at least one processor adapted to store data defining a plurality of relationships, each respective relationship being associated with a respective mixture of concrete, a respective temperature, and a respective relative humidity, each respective relationship showing strength as a function of age for the corresponding mixture when cured at the respective temperature and the respective relative humidity, receive the third measurement of temperature and the fourth measurement of humidity of the specimen of concrete in the test cylinder, receive a fifth measurement of strength of the specimen of concrete in the test cylinder, identify, from among the plurality of relationships, a first relationship showing strength as a function of age of the specimen of concrete, based on the third measurement of temperature, the fourth measurement of humidity, and the fifth measurement of strength, identify a mixture based on the first relationship, receive the first measurement of a temperature and a second measurement of humidity, determine a second relationship showing strength as a function of age of the quantity of concrete in the structure, based on the first measurement of a temperature and a second measurement of humidity, and generate a prediction of a final strength of the quantity of concrete based on the second relationship.

In accordance with another embodiment, a method is provided. Data defining a plurality of relationships, each respective relationship being associated with a respective mixture of concrete, a respective temperature, and a respective relative humidity, each respective relationship showing strength as a function of age for the corresponding mixture when cured at the respective temperature and the respective relative humidity, is stored. A first measurement of temperature and a second measurement of humidity of a quantity of concrete in a structure, the quantity of concrete associated with a batch of concrete comprising a particular mixture, are received. A third measurement of temperature and a fourth measurement of humidity of a specimen of concrete in a test cylinder, the specimen of concrete being associated with the batch, are received. A fifth measurement of strength of the specimen of concrete in the test cylinder is received. A first relationship showing strength as a function of age of the specimen of concrete, based on the third measurement of temperature, the fourth measurement of humidity, and the fifth measurement of strength is identified from among the plurality of relationships. A mixture is identified based on the first relationship. A second relationship showing strength as a function of age of the quantity of concrete in the structure is determined based on the first measurement of temperature and the second measurement of humidity. A prediction of a final strength of the quantity of concrete is generated based on the second relationship.

Advantageously, systems, apparatus, and methods described herein include efficient curing by sealing in moisture, monitoring maturity by measuring temperature, geolocating the tests, and using a range of different sensors to estimate characteristics such as strength in real time. Advantageously, all data is communicated via a network such as the Internet to a consolidated database storing data covering areas as specific as particular project sites to entire countries.

These and other advantages of the present disclosure will be apparent to those of ordinary skill in the art by reference to the following Detailed Description and the accompanying drawings.

DETAILED DESCRIPTION

Figure 1:
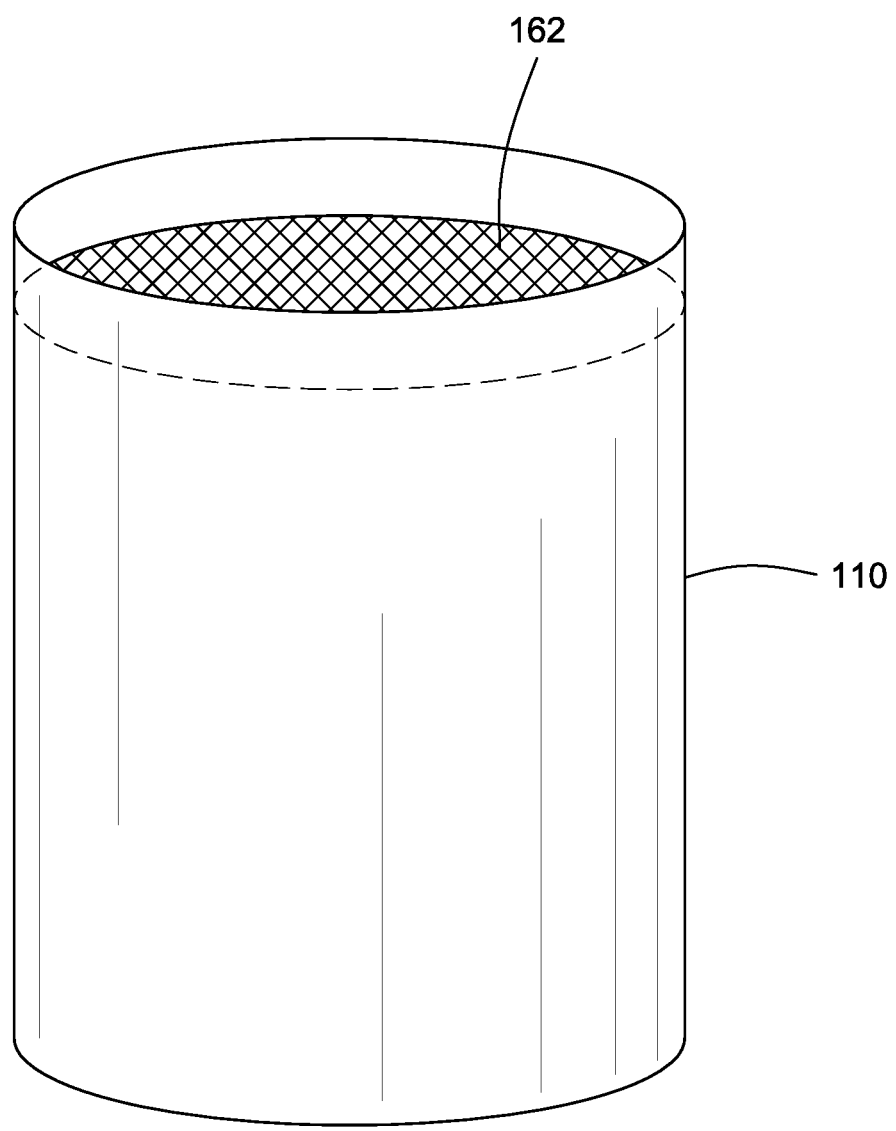
FIG. 1 shows an exemplary test cylinder containing a test specimen of concrete.

In accordance with standards set forth in ASTM C31 (Standard Practice for Making and Curing Concrete Test Specimens in the Field), the compressive strength of concrete is measured to ensure that concrete delivered to a project meets the requirements of the job specification and for quality control. In order to test the compressive strength of concrete, cylindrical test specimens are cast in test cylinders and stored in the field until the concrete hardens. FIG. 1 shows an exemplary test cylinder 110 containing a test specimen of concrete 162.

The U.S. concrete industry tests approximately twenty (20) million test cylinders annually. The cylinders are first field cured for one or two days and then moved to a laboratory for analysis. Typically, it is necessary to wait twenty-eight (28) days before certain characteristics of the concrete, including a key strength quality, can be determined.

The concrete testing procedure is complicated by other factors. For example, the concrete should be kept moist to cure well; however, field conditions sometimes make it difficult to ensure that the concrete remains moist. In addition, due to the variety and unpredictability of field conditions, it is sometimes difficult to know when a test cylinder is strong enough to be moved.

The smart cap system described herein advantageously facilitates a determination of maturity and strength in real time, and also enables a user to determine when the test cylinder can be moved safely. The smart cap system also advantageously provides, for a contractor, real-time measures of the concrete specimen to determine whether it is strong enough to demold.

Advantageously, the smart cap system includes a geolocation capability that allows a user to know the location of the test cylinders at all times (where the concrete is poured, where the test cylinder is placed while curing, etc.). The geolocation function also enables a user to associate each test cylinder to a particular element of a construction project.

Advantageously, the smart cap system described herein enables a user to detect potential problems, such as additions of water to a batch of concrete and any resulting weakening of the concrete.

Advantageously, the smart cap system described herein makes it possible for a user to monitor and control quality versus location across projects, states, and countries; quality versus location may be visually and quantitatively available based on the data collected from various smart cap systems.

Advantageously, the smart cap system described herein can help make both the production of concrete and the use of concrete in building more efficient, and thereby contribute to making these industries more efficient.

Advantageously, systems, apparatus, and methods described herein include efficient curing by sealing in moisture, monitoring maturity by measuring temperature, geo-locating the tests, and using a range of different sensors to estimate characteristics such as strength in real time. Advantageously, all data is communicated via a network such as the Internet to a consolidated database storing data covering areas as specific as particular project sites to entire countries.

Figure 2A:
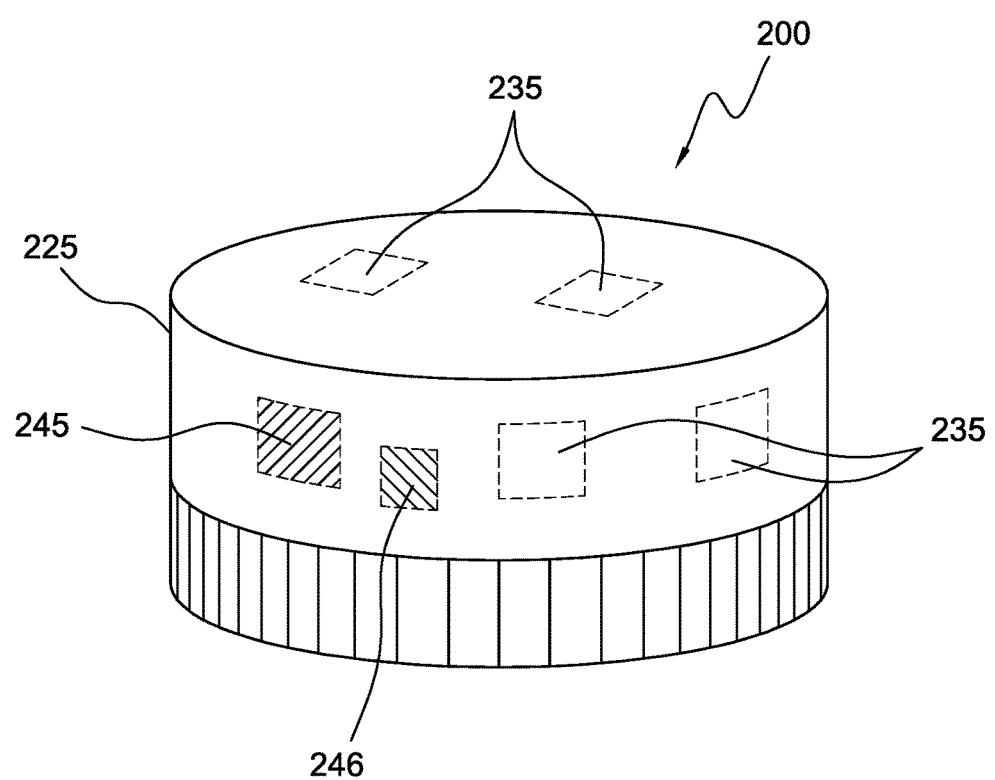
FIG. 2A shows a top view of a smart cap system in accordance with an embodiment.

In accordance with an embodiment, a smart cap is placed on a standard test cylinder and used to test various properties of a concrete mixture contained in the test cylinder. FIG. 2A shows a top view of a smart cap system 200 in accordance with an embodiment. Smart cap system 200 includes a cap 225, which may be made of plastic, for example. In other embodiments, cap 225 may comprise another material, such as ABS, PVC, Teflon, hard rubber (such as Ebonite), or any polymeric material that is, for example, relatively rigid but somewhat deformable. In another embodiment, cap 225 comprises a material that may be 3D printed or injection molded.

Smart cap system 200 also includes one or more sensors 235, which may be attached to an internal surface of the cap, or may be embedded in the internal surface of the cap, for example. In other embodiments, sensors 235 may be placed in other locations on or within a cap. Sensors 235 may include a variety of different types of sensors including temperature sensors, humidity sensors, chronometers, heat flow sensors capable of measuring heat and/or heat flow, motion sensors, pH sensors, location detectors, GPS sensors, etc. One or more of sensors 235 may include an accelerometer, a triangulation sensor, a thermoelectric heat flow sensor, a salinity sensor, an inductance sensor, an impedance or resistivity sensor, a sonic sensor, a pressure sensor, a conductivity sensor, an elevation sensor, etc. In one embodiment, a salinity sensor may include a chloride ion electrode, for example.

One or more of sensors 235 may include a thermoelectric sensor cooler, such as a Peltier plate. One or more of sensors 235 may include a macro fiber composite (WC) sensor for detecting motion.

In one embodiment, smart cap system 200 includes a temperature sensor that is adapted to penetrate (or be embedded within) the concrete inside the cylinder, or is adapted to be connected into concrete via a conducting copper rod, or is adapted to be positioned close to the surface of the concrete in the cylinder and to measure temperature (due to the walls of smart cap system 200 being insulated and the fact the moist warm air rises).

In another embodiment, smart cap system 200 includes a humidity sensor that is adapted to be positioned close to the concrete surface and measure the concrete surface humidity.

In another embodiment, smart cap system 200 includes a capillary sensor that penetrates the concrete by several centimeters and senses the internal humidity of the concrete, which changes as hydration occurs and microstructure is formed, and shows sensitivity to key strength determining variables such as water-to-cement and water-to-cementitious ratios.

In another embodiment, smart cap system 200 includes an accelerometer which functions as a motion sensor.

Smart cap system 200 also includes a communication device 245 adapted to transmit measurement data to a communication network or to another device. Communication device 245 may include a transmitter, a receiver, a transceiver, etc. In other embodiments, communication device 245 may also include other components such as a processing device, a memory, etc. For example, communication device 245 may control one or more sensors within smart cap system 200, and may transmit measurement data to a remote device or computer system, directly or via a network.

Each sensor has its own unique ID that is transmitted and can be relationally linked to a unique concrete batch ID, with recorded batch contents.

In the illustrative embodiment, smart cap system 200 includes a radio frequency identification (RFID) device 246. RFID device 246 transmits a unique identifier associated with smart cap system 200. For example, RFID device 246 may be attached to, or embedded in, an internal or external surface of cap 225.

In one embodiment, RFID device 246 or the unique sensor ID facilitates the association of smart cap system 200 with a particular batch of concrete. For example, after a truck carrying a batch of a concrete mixture arrives at a construction site, concrete is poured from the truck into a test cylinder, and smart cap system is placed on the test cylinder, in the manner described above. A technician at the construction site may use a scanning device (e.g., a specialized scanning device, a cell phone, etc.) to scan an identifying barcode associated with the batch (e.g., a barcode affixed on the inside/outside of the truck) to identify the batch. Separately, the technician may scan smart cap system 200 (now located on the test cylinder) to obtain a unique RFID. The batch identifying information and the unique RFID or sensor ID information are transmitted to a remote processor, which associates the test cylinder with the batch based on the batch identifying information and the unique RFID or sensor ID information.

Figure 2B:
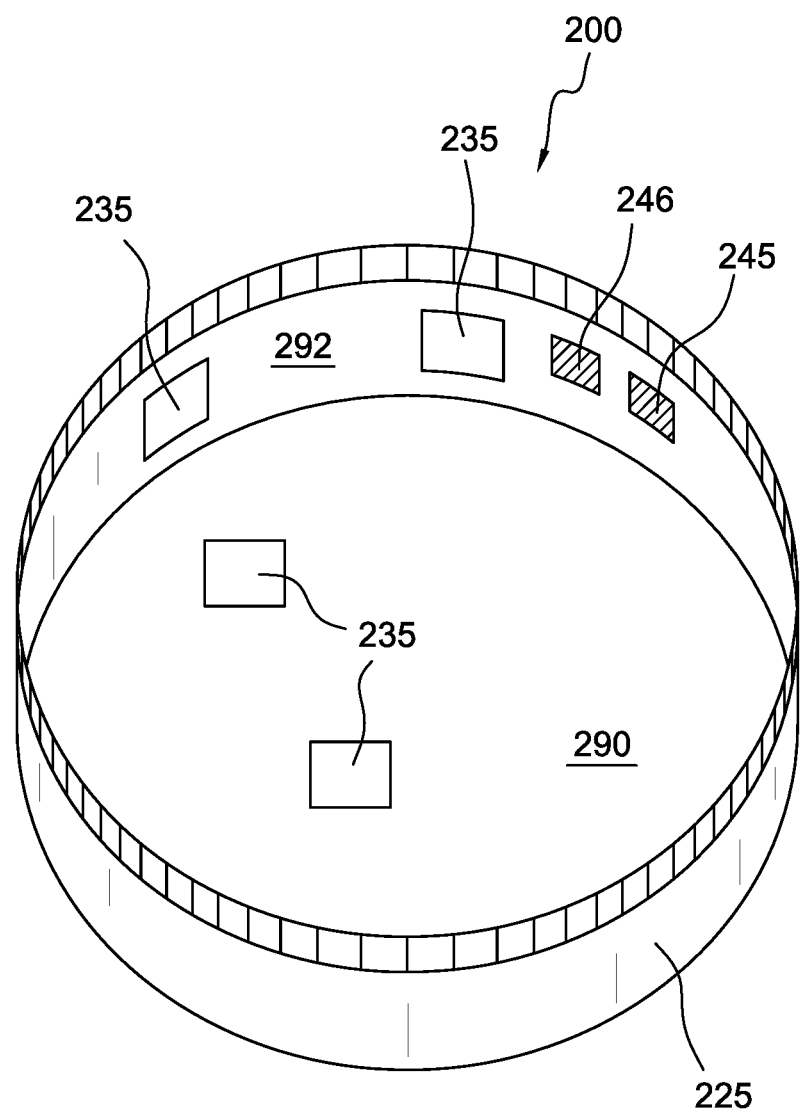
FIG. 2B shows a bottom view of smart cap system in accordance with an embodiment.

FIG. 2B shows a bottom view of smart cap system 200 in accordance with an embodiment. Smart cap system 200 includes internal surfaces 290 and 292. Sensors 235 are attached to internal surfaces 290 and/or 292. Alternatively, sensors 235 may be embedded in internal surfaces 290, 292. For example, the internal surfaces 290, 292 may comprise a material such as a plastic material; the sensors may be embedded in the plastic material.

Figure 2C:
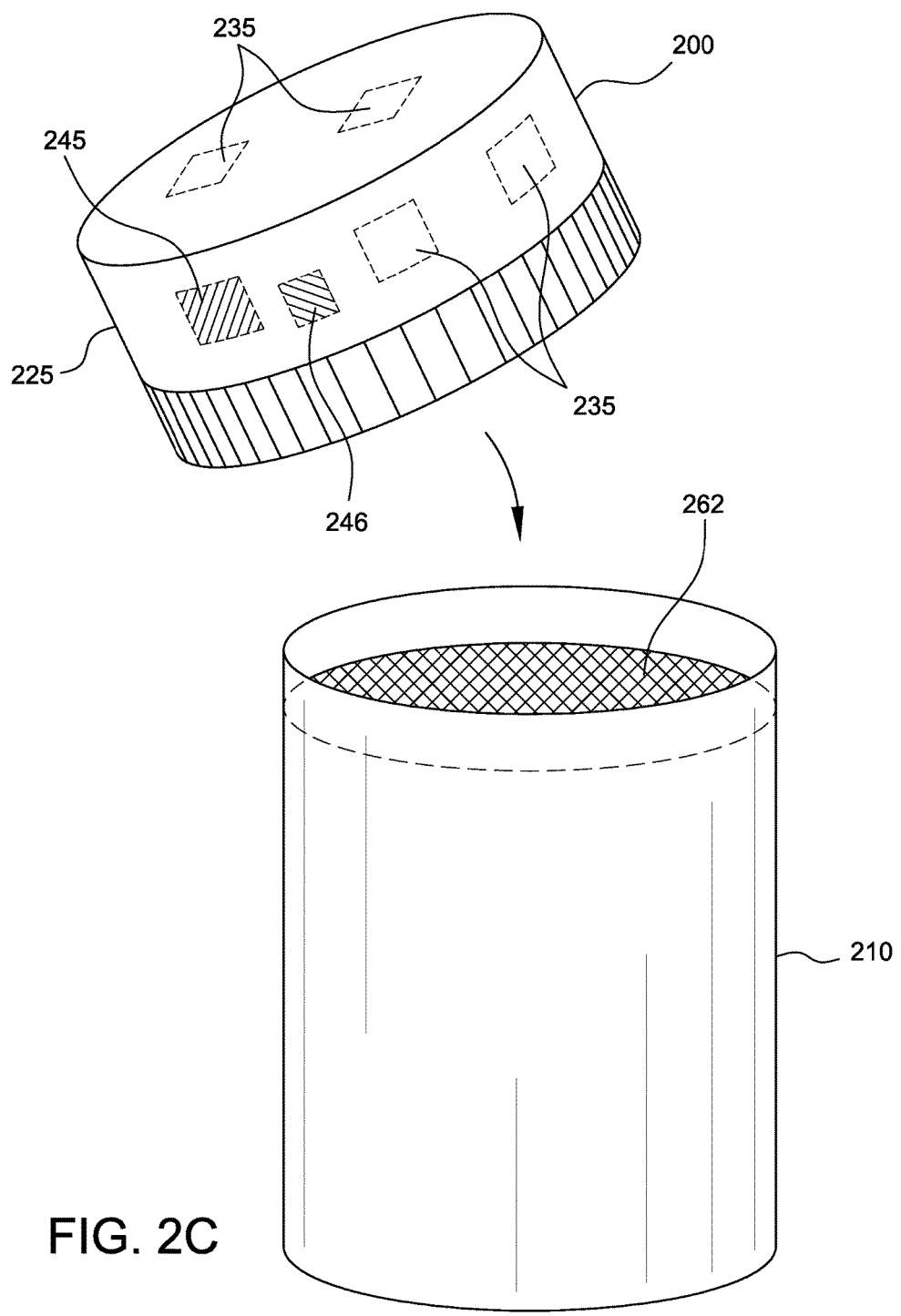
FIG. 2C shows a smart cap system and a test cylinder in accordance with an embodiment.

In accordance with an embodiment, smart cap system 200 is placed on a test cylinder, as shown in FIG. 2C. In one embodiment, test cylinder 210 is a standard-sized test cylinder. Thus, test cylinder 210 may be a 4×8-inch cylinder or a 6×12-inch cylinder, for example. Cap 225 of smart cap system 200 is adapted to fit onto a standard test cylinder. Thus, in one embodiment, the cap 225 is adapted to fit onto a 4×8-inch cylinder; in another embodiment, the cap 225 cap is adapted to fit onto a 6×12-inch cylinder. Cap 225 may be circular in shape, for example.

In another embodiment, the cap may be adapted to fit onto container shaped as a 150 mm or 200 mm cube.

In the illustrative embodiment, cap 225 has a top section and a side section that fits around and outside the rim of the test cylinder. Other designs may be used.

In other embodiments, other shapes and sizes may be used. Thus, in other embodiments, a smart cap system may have other (non-standard) sizes and may include a cap adapted to fit onto a triangular, square, rectangular, hexagonal, octagonal, or oval-shaped container of concrete, for example. A smart cap system may have a cap having any shape such as triangular, square, rectangular, oval-shaped, hexagonal, octagonal, etc. The cap may be adapted to fit onto a container of any size or dimensions.

Figure 2D:
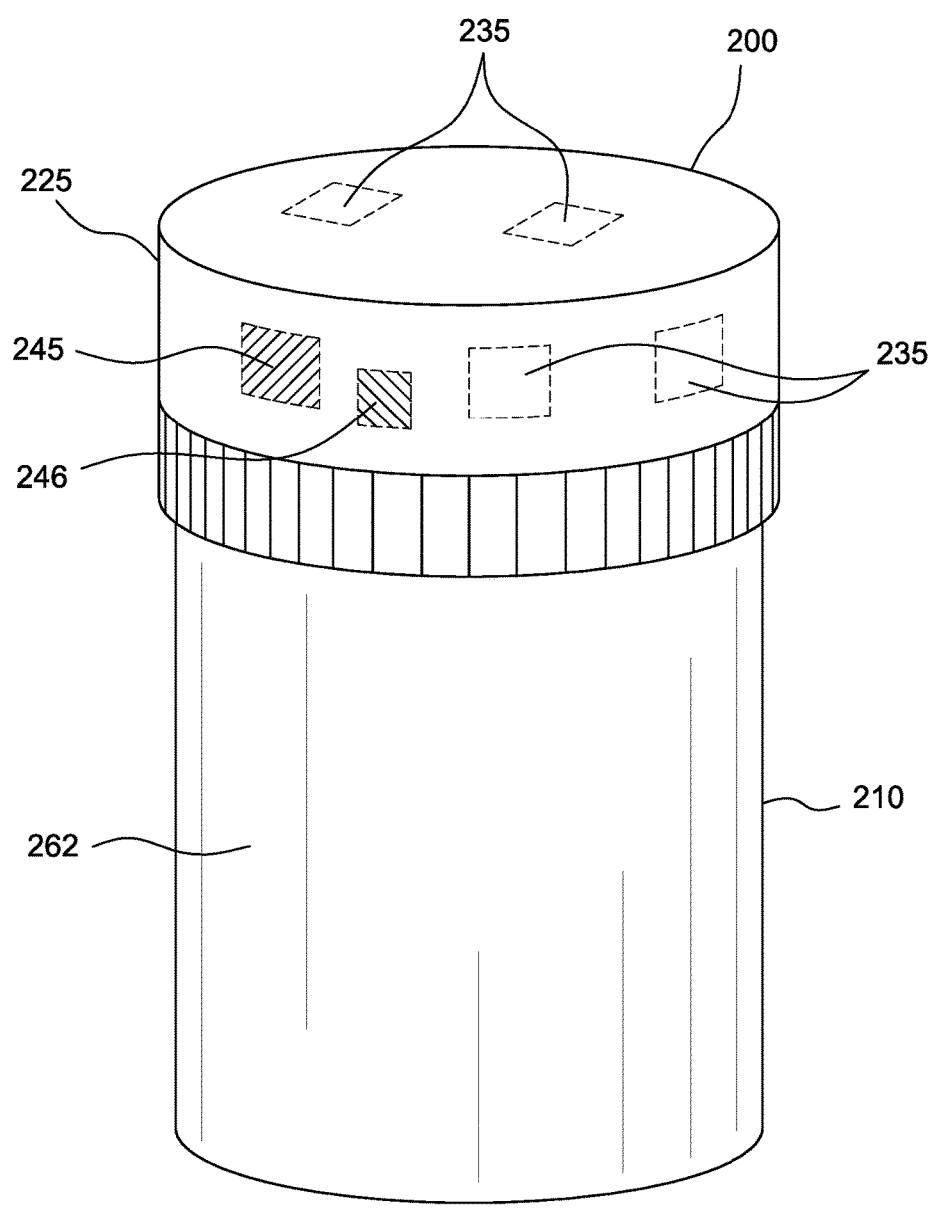
FIG. 2D shows a smart cap system fitted onto a test cylinder in accordance with an embodiment.

In accordance with an embodiment, a specimen of concrete 262 is placed in test cylinder 210, as shown in FIG. 2C. After the concrete is placed into test cylinder 210, smart cap system 200 is placed on test cylinder 210. FIG. 2D shows smart cap system 200 fitted onto test cylinder 210 after concrete has been placed in the cylinder in accordance with an embodiment.

In accordance with the standards set forth in ASTM C31, test cylinder 210 (with smart cap system 200 thereon) is now placed in a selected location for a predetermined period of time. During this period, the concrete sets.

While test cylinder 210 (and smart cap system 200) remains in the selected location, sensors 235 obtain measurements related to the concrete specimen 262. For example, sensors 262 may obtain temperature measurements, humidity measurements, etc. Sensors 235 may also obtain measurements regarding motion and location of test cylinder 210. Smart cap system 200 may transmit measurement data to a communication network or to another device.

Figure 3:
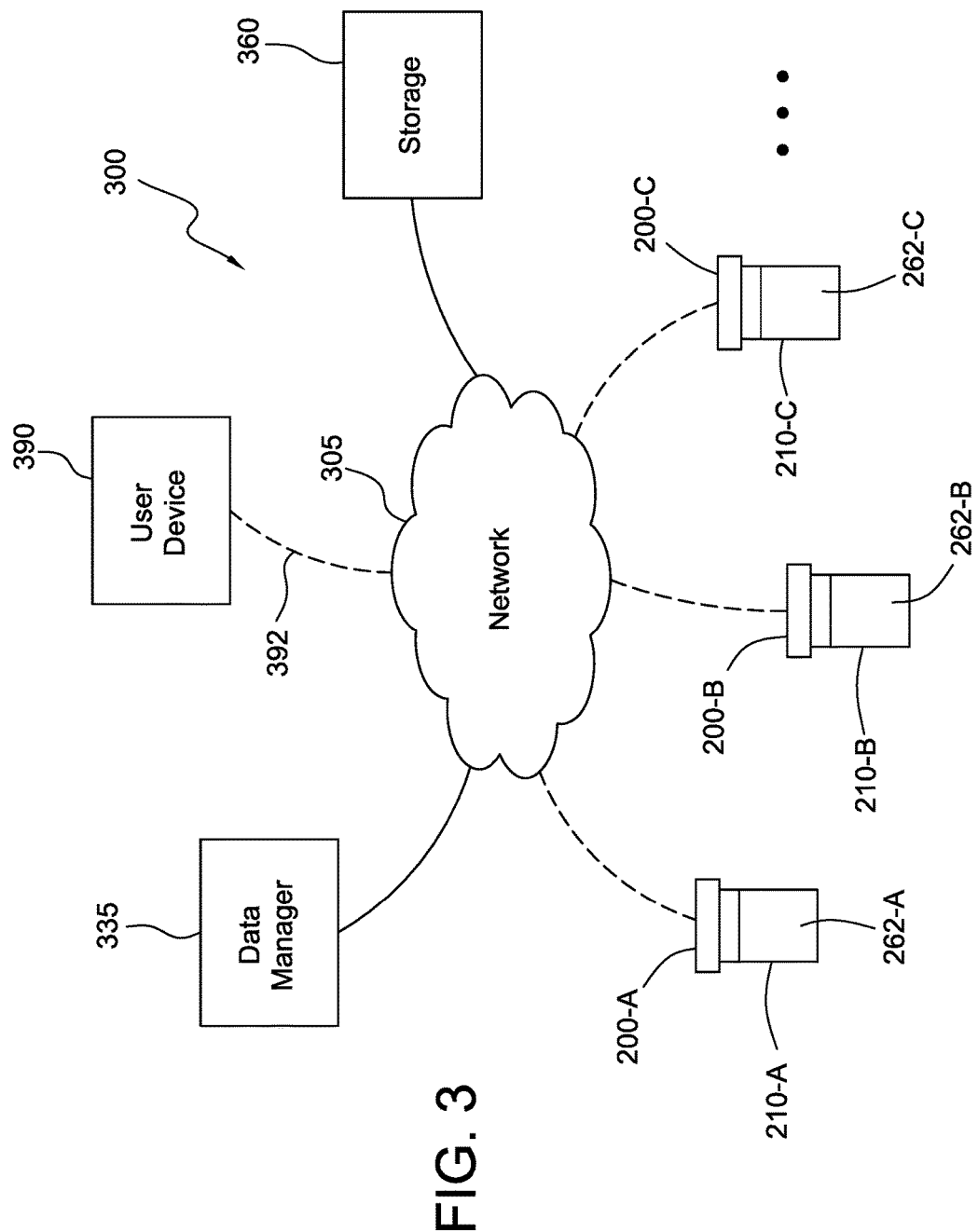
FIG. 3 shows a communication system in accordance with an embodiment.

In accordance with an embodiment, smart cap system 200 communicates with a processing device via a network. FIG. 3 shows a communication system in accordance with an embodiment. Communication system 300 includes a network 305, a data manager 335, a storage 360, and a plurality of smart cap systems 200-A, 200-B, 200-C, etc. Smart cap systems 200-A, 200-B, 200-C are disposed on respective test cylinders 210-A, 210-B, 210-C, that hold respective specimens of concrete 262-A, 262-B, 262-C. Each smart cap system 200 obtains measurements related to a respective specimen of concrete. Each smart cap system 200 transmits measurement data to data manager 335 via network 305. Each smart cap system 200 may also transmit an identifier uniquely identifying itself. For example, an RFID tag embedded in each smart cap system may transmit identification information. Communication network 300 may include any number of smart cap systems.

In one embodiment, multiple smart cap systems 200 may be located at a single location (e.g., a single construction site). In another embodiment, multiple smart cap systems 200 may be located at multiple locations (e.g., at multiple construction sites).

Communication system 300 also includes a user device 390, which may be a personal computer, laptop device, tablet device, cell phone, or other processing device which is located at a construction site and used by a technician at the site. User device 390 is linked to network 305 via a link 392.

Data manager 335 receives measurement data from one or more smart cap systems 200 and analyzes the measurement data. Data manager 335 may generate predictions concerning the behavior of one or more concrete specimens. For example, data manager 335 may receive temperature, humidity, heat flow, motion, and/or location, data from smart cap system 200-A and, based on the measurement data, generate predictions regarding the water-to-cementitious ratio, durability, strength, slump, maturity, etc., of the concrete specimen 262-A in cylinder 210-A. Similarly, for example, data manager 335 may receive temperature, humidity, heat flow, motion, and/or location, data from smart cap system 200-B and, based on the measurement data, generate prediction data regarding the water-to-cementitious ratio, durability, strength, slump, maturity, etc., of the concrete specimen 262-B in cylinder 210-B. In one embodiment, the measurement data received by data manager 335 is provided to a real-time model to project setting behavior and strength for an entire batch of concrete. In another embodiment, the measurement data is continually subject to statistical analysis to generate real-time projections, control charts, etc. Data manager 335 may store prediction data in storage 360. For example, prediction data may be stored in a database. Other data structures may be used to store prediction data.

In one embodiment, data manager 335 may transmit measurement data and/or prediction information relating to water-to-cementitious ratio, durability, strength, slump, maturity, etc. to a user device such as user device 390 to enable a technician to access and view the information. For example, user device 390 may display measurement data and/or prediction data on a web page, or in another format.

Figure 4:
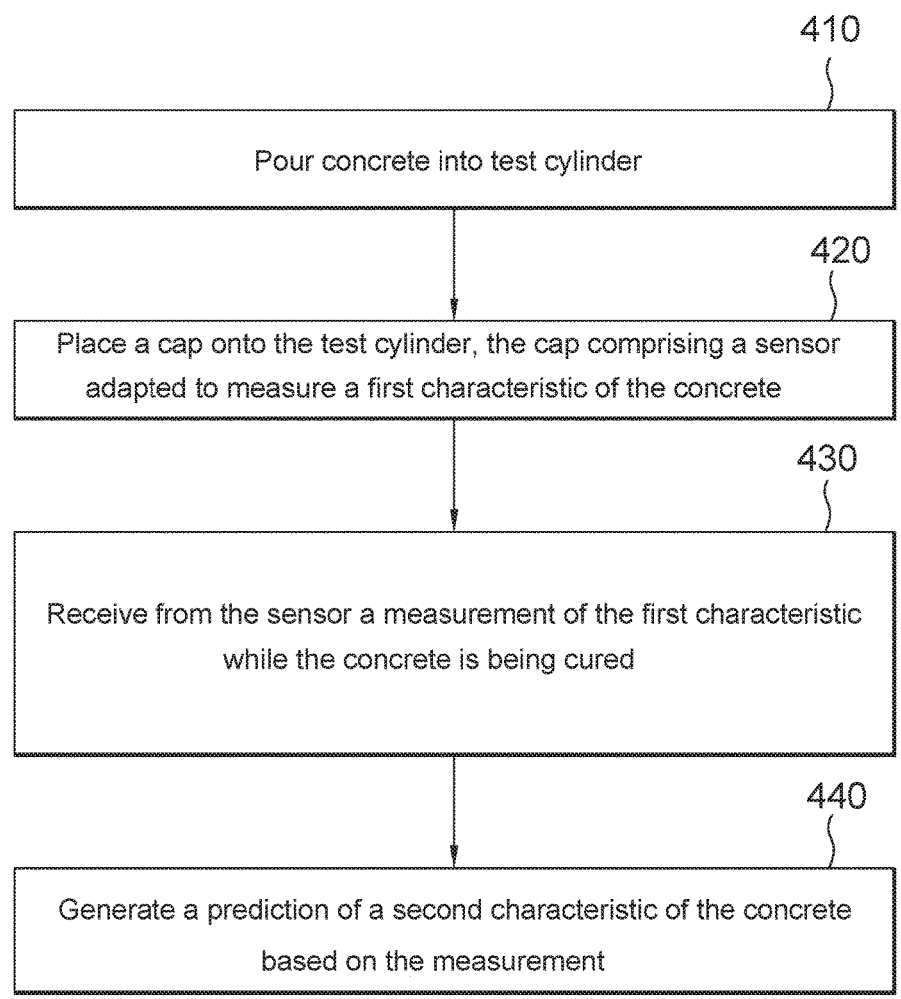
FIG. 4 is a flowchart of a method in accordance with an embodiment.

FIG. 4 is a flowchart of a method in accordance with an embodiment. At step 410, concrete is poured into a test cylinder. Referring to FIG. 2C, for example, concrete 262 is poured into cylinder 210.

At step 420, a cap is placed onto the test cylinder, the cap comprising a sensor adapted to measure a first characteristic of the concrete. In the illustrative embodiment of FIG. 2D, smart cap system 200 is placed onto cylinder 210. Smart cap system 200 includes at least one sensor, which may be, for example, a temperature sensor.

In one embodiment, smart cap system 200 receives batch proportion data (i.e., data indicating the components of a particular batch of concrete and the quantities/proportions of the various components) from the mixing truck when the concrete is poured into the cylinder.

In the illustrative embodiment, cylinder 210 and smart cap system 200 are placed in a carefully selected location for a predetermined time period, in accordance with the standards set forth in ASTM C31.

At step 430, a measurement of the first characteristic is received from the sensor while the concrete is concrete is being cured. While the concrete 262 in cylinder 210 is being cured, sensors 235 of smart cap system 200 obtain measurements of various characteristics of the concrete. For example, a temperature sensor may obtain a measurement of the temperature of concrete 262. Referring to FIG. 3, smart cap system 200 transmits the measurement data obtained by sensors 235 to data manager 335 via network 305.

At step 440, a prediction of a second characteristic of the concrete is generated based on the measurement. For example, data manager 335 may generate a prediction regarding the concrete's maturity based on the temperature measurement. Similarly, data manager 335 may generate a prediction regarding the concrete's water-to-cementitious ratio, durability, strength, slump, etc. based on one or more measurements.

Figure 5:
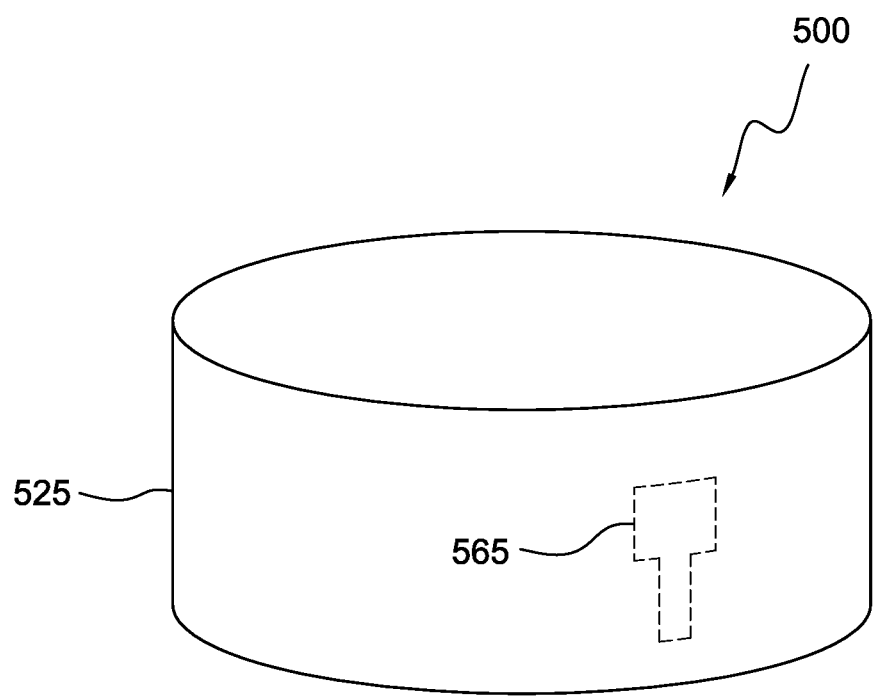
FIG. 5 shows a smart cap system in accordance with an embodiment.

In accordance with another embodiment, a smart cap system includes a capillary sensor. FIG. 5 shows a smart cap system 500 in accordance with an embodiment. Smart cap system 500 includes a cap 525 and a capillary sensor 565. Capillary sensor 565 is attached to an internal surface of cap 525.

Figure 6:
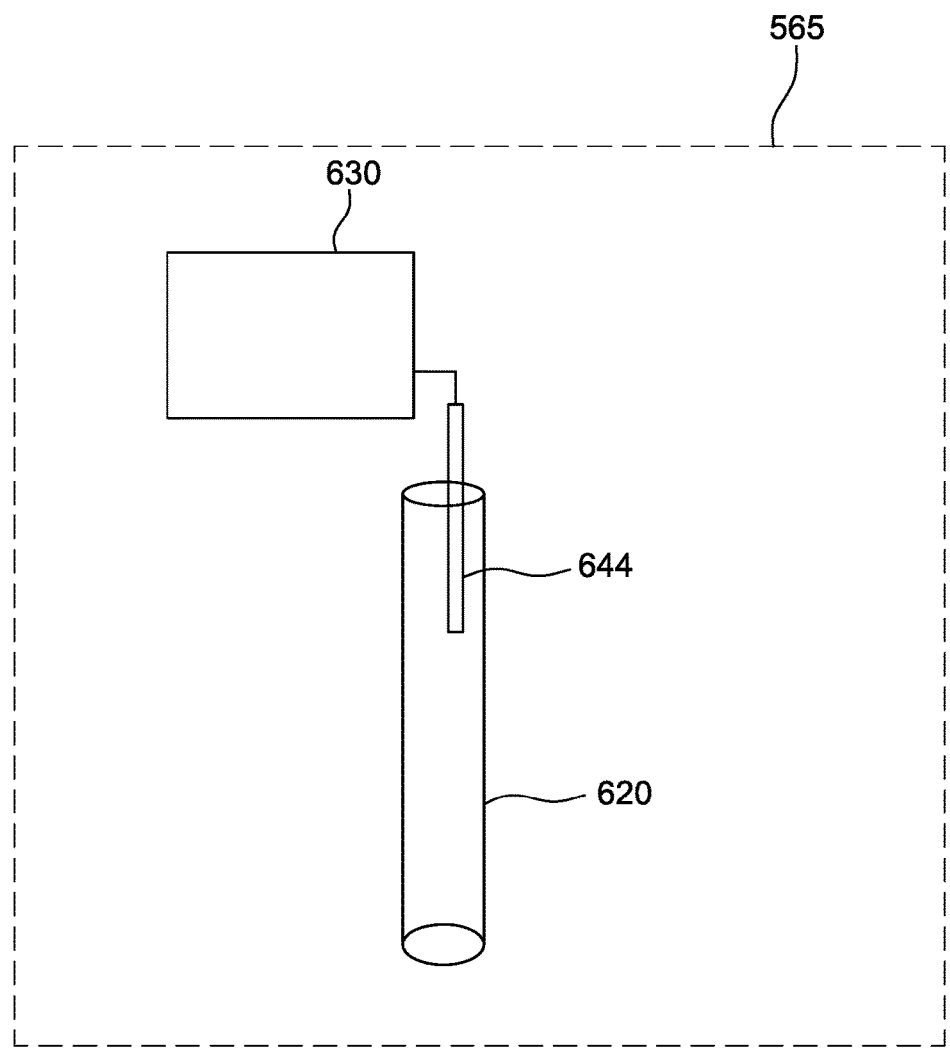
FIG. 6 shows components of capillary sensor 565 in accordance with an embodiment.

FIG. 6 shows components of capillary sensor 565 in accordance with an embodiment. Capillary sensor 565 includes a tube 620, a processing device 630, and a measuring device 644. Tube 620 is sufficiently thin to allow capillary action to draw a fluid up into the tube. Processing device 630 may include a computer, for example. Measuring device 644 may comprise any type of measuring device for measuring any type of data; for example, measuring device 644 may comprise a thermometer, a pH sensor, etc. Measuring device 644 may transmit measurement data to processing device 630. Processing device 630 may also include a transmitter for transmitting data via a wireless network, for example.

Figure 7A:
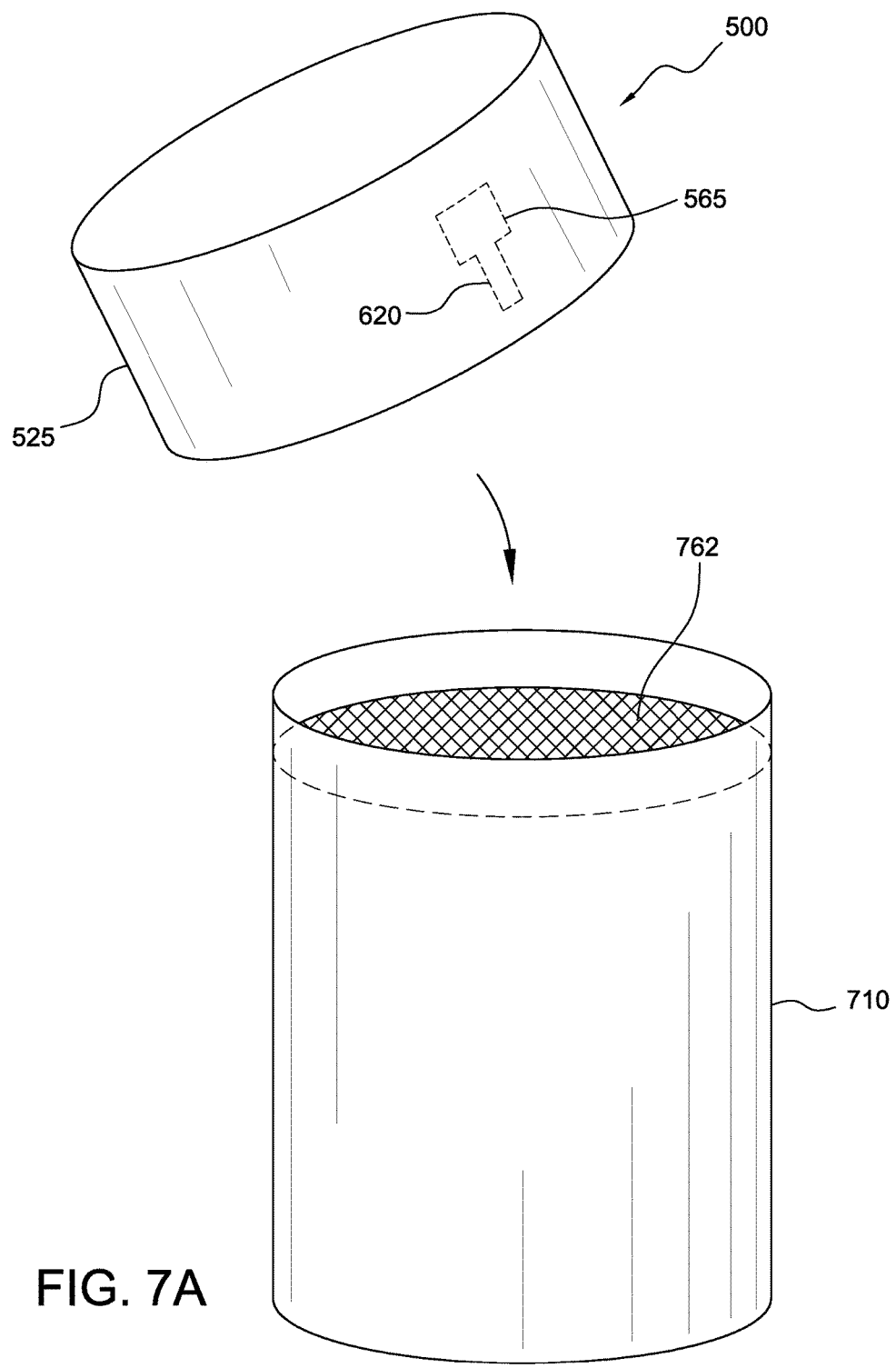
FIG. 7A shows a smart cap system and a test cylinder in accordance with an embodiment.
Figure 7B:
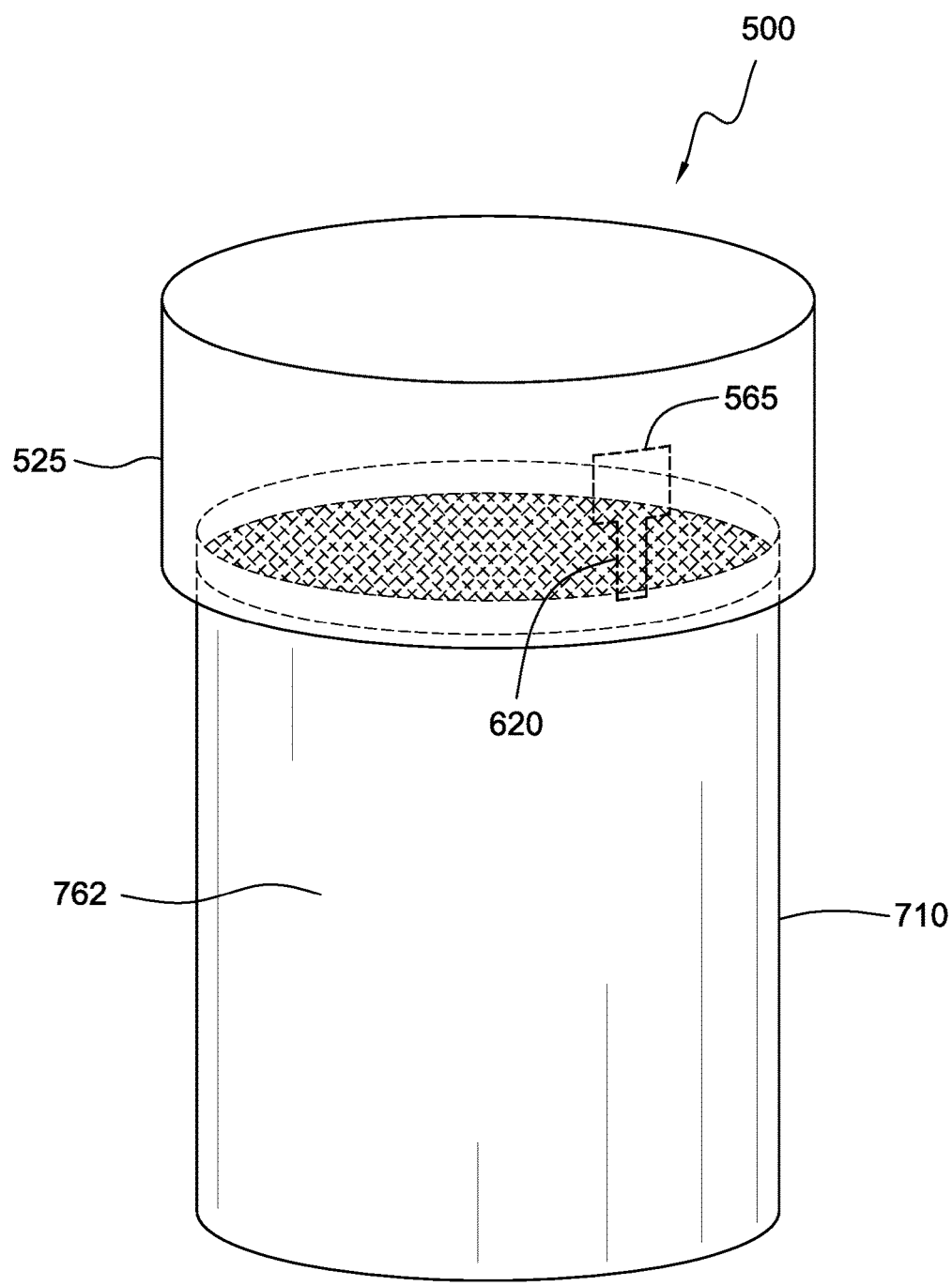
FIG. 7B shows a smart cap system fitted on a cylinder in accordance with an embodiment.

In accordance with an embodiment illustrated in FIG. 7A, smart cap system 500 is placed on a test cylinder 710 after concrete 762 has been poured into cylinder 710. Referring to FIG. 7B, after smart cap system 500 is fitted on cylinder 710, tube 620 comes into contact with the surface of concrete 762, and capillary action causes water in the concrete to rise up through the tube 620 to measuring device 644. Measuring device 644 measures one or more characteristics of the water. For example, measuring device 644 may measure the temperature of the water, humidity of water (which could be less than 100% due to meniscus formation), the pH level of the water, etc. Measuring device 644 provides measurement data to processing device 630, which may determine a characteristic of concrete 762 based on the measurement data. Processing device 630 may also transmit measurement data to another device via a network.

Figure 8:
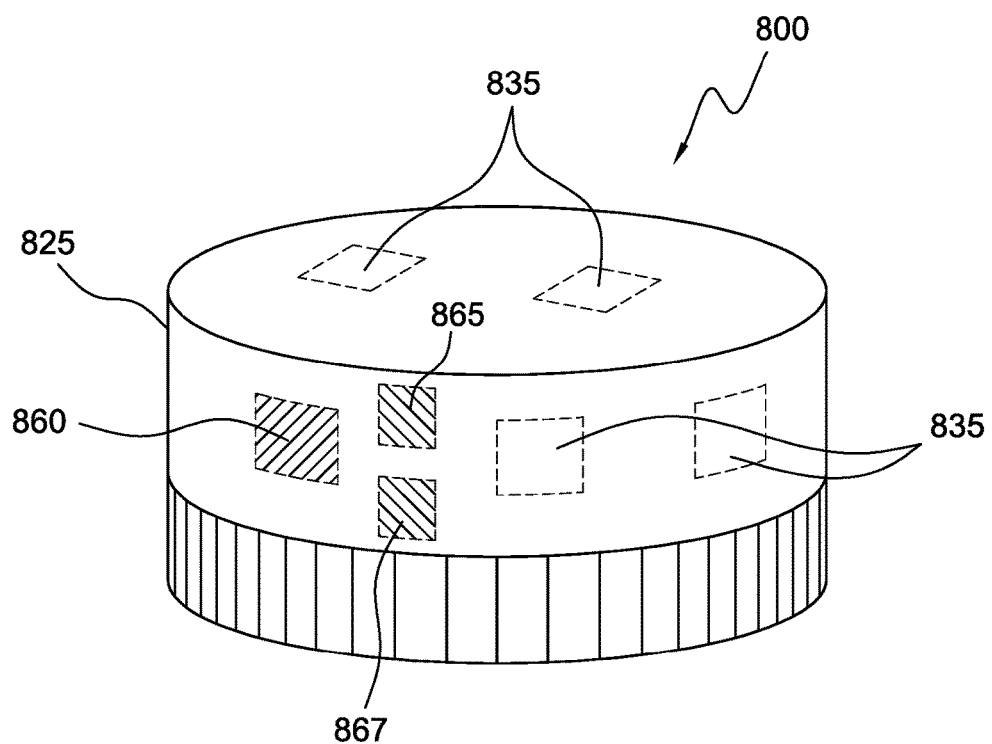
FIG. 8 shows a smart cap in accordance with another embodiment.

FIG. 8 shows a smart cap in accordance with another embodiment. Smart cap system 800 includes a cap 825 and sensors 835, which are similar to cap 225 and sensors 235 described above. For example, sensors 835 may include temperature sensors, humidity sensors, chronometers, heat flow sensors capable of measuring heat and/or heat flow, motion sensors, pH sensors, location detectors, MFC sensors, GPS sensors, a capillary sensor, etc. Smart cap system 800 also includes a processor 860 communicatively coupled to sensors 835, a memory 865, and a transmitter 867. Smart cap system 800 may be placed on a test cylinder containing a specimen of concrete in the manner described above, and sensors 835 may obtain measurement data relating to the concrete. Sensors 835 transmit measurement data to processor 860. Measurement data may be stored in memory 865. Processor 860 may generate one or more predictions with respect to the maturity, strength, slump, etc., of the concrete specimen based on the measurement data. Processor 860 may cause transmitter 867 to transmit the measurement data and/or the prediction data to another device, such as data manager 335, via a network.

Figure 9:
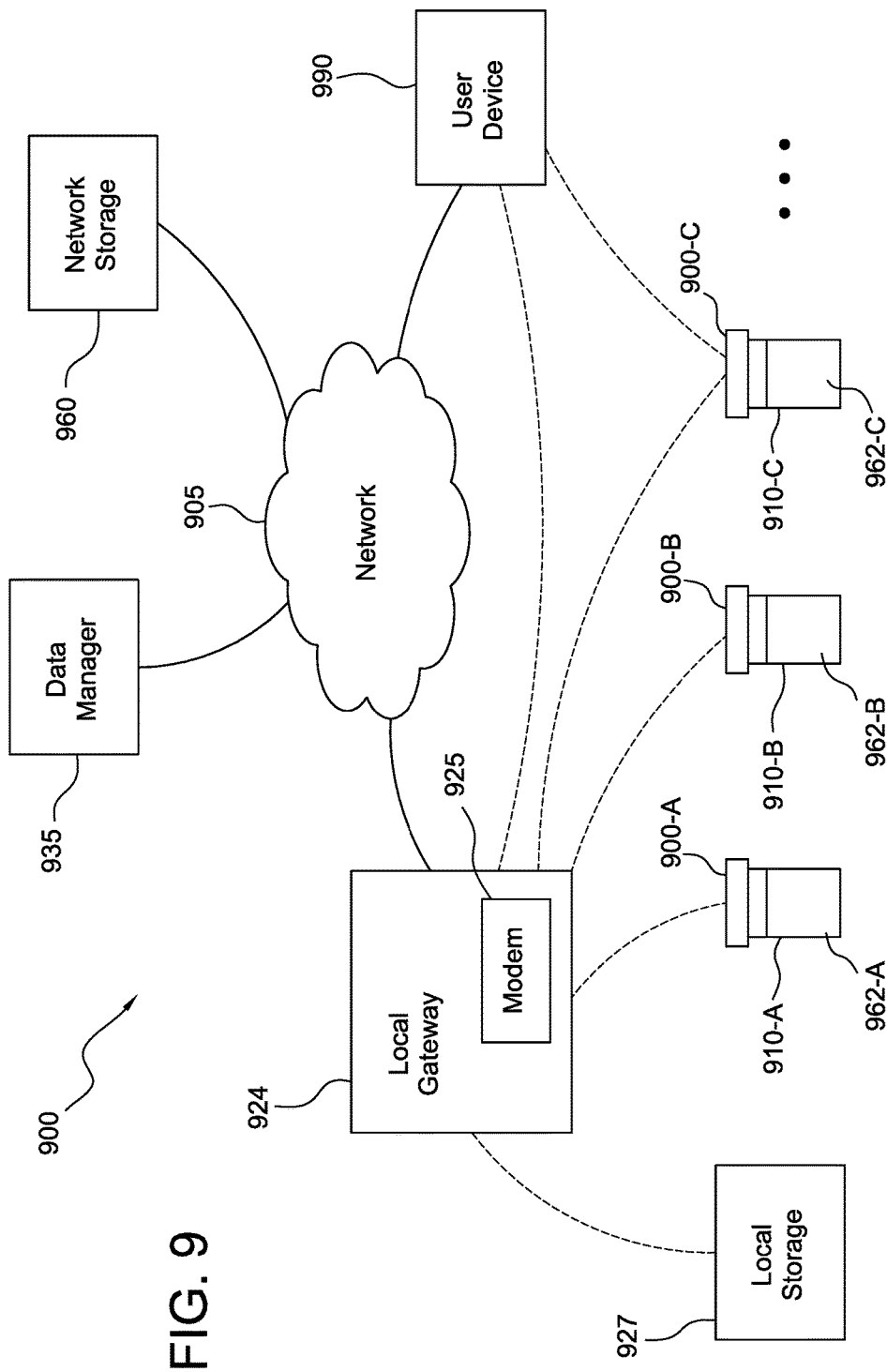
FIG. 9 shows a communication system in accordance with an embodiment.

In accordance with another embodiment, a smart cap system communicates with a processing device and/or a remote storage via a wireless modem and an Internet cloud network or other Internet-based communication network. FIG. 9 shows a communication system in accordance with an embodiment. Communication system 900 includes a network 905, which includes the Internet, a data manager 935, and a network storage 960.

Communication system 900 also includes a local gateway 924, which is connected to network 905. Local gateway 924 includes a modem 925, which may be a wireless modem, for example. Local gateway 924 is linked to a plurality of smart cap systems 900-A, 900-B, 900-C, etc. Local gateway 924 is also linked to a local storage 927. Local gateway 924 may from time to time store data, such as measurement data received from smart cap systems 900, in local storage 927. Local gateway 924 and local storage 927 may be located at or near a construction site, for example.

Smart cap systems 900-A, 900-B, 900-C are disposed on respective test cylinders 910-A, 910-B, 910-C, that hold respective specimens of concrete 962-A, 962-B, 962-C. Using methods and apparatus similar to those described above, each smart cap system 900 obtains measurements related to a respective specimen of concrete. Each smart cap system 900 transmits measurement data to data manager 935 via local gateway 924 and network 905. For example, each smart cap system 900 may transmit measurement data wirelessly to local gateway 924, which transmits the measurement data to data manager 935 via network 905. Each smart cap system 900 may also transmit an identifier uniquely identifying itself. For example, an RFID tag embedded in each smart cap system may transmit identification information. Communication system 900 may include any number of smart cap systems.

In one embodiment, multiple smart cap systems 900 may be located at a single location (e.g., a single construction site). In another embodiment, multiple smart cap systems 900 may be located at multiple locations (e.g., at multiple construction sites).

Communication network 900 also includes a user device 990, which may be a personal computer, laptop device, tablet device, cell phone, or other processing device which is located at a construction site and used by a technician at the site. User device 990 may communicate with network 905, with local gateway 924, and/or with other devices within communication system 900.

Data manager 935 receives measurement data from one or more smart cap systems 900 and analyzes the measurement data. Data manager 935 may generate predictions concerning the behavior of one or more concrete specimens. For example, data manager 935 may receive temperature, humidity, heat flow, motion, and/or location, data from smart cap system 900-A and, based on the measurement data, generate predictions regarding the water-to-cementitious ratio, durability, strength, slump, maturity, etc., of the concrete specimen 962-A in cylinder 910-A. Similarly, for example, data manager 935 may receive temperature, humidity, heat flow, motion, and/or location, data from smart cap system 900-B and, based on the measurement data, generate prediction data regarding the water-to-cementitious ratio, durability, strength, slump, maturity, etc., of the concrete specimen 962-B in cylinder 910-B. In one embodiment, the measurement data received by data manager 935 is provided to a real-time model to project setting behavior and strength for the entire batch of concrete. In another embodiment, the measurement data is continually subject to statistical analysis to generate real-time projections, control charts, etc. Data manager 935 may store prediction data in network storage 960. For example, prediction data may be stored in a database. Other data structures may be used to store prediction data.

In one embodiment, data manager 935 may transmit measurement data and/or prediction information relating to water-to-cementitious ratio, durability, strength, slump, maturity, etc. to a user device such as user device 990 to enable a technician to access and view the information. For example, user device 990 may display measurement data and/or prediction data on a web page, or in another format.

In one embodiment, network storage 960 may comprise a cloud storage system. Data obtained by sensors on smart cap systems 900-A, 900-B, 900-C, may be transmitted to and saved in network storage 960 in real-time. A cloud implementation such as that illustrated by FIG. 9 may allow data from projects in multiple regions or multiple countries to be auto-consolidated in a single database.

Figure 10A:
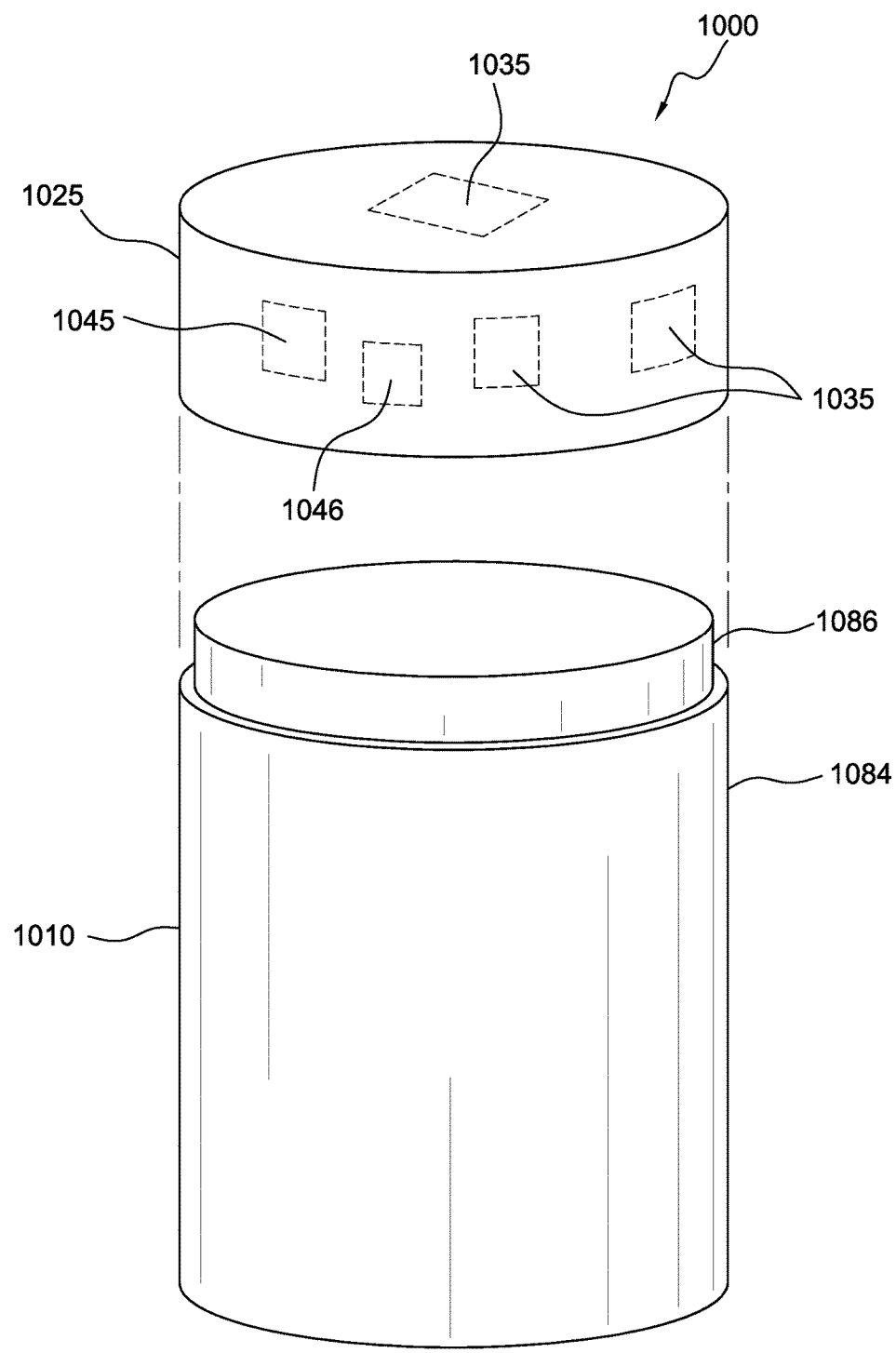
FIG. 10A shows a smart cap system and a test cylinder in accordance with another embodiment.

FIG. 10A shows a smart cap system 1000 in accordance with another embodiment. Smart cap system 1000 includes a cap 1025, and one or more sensors 1035, which may include various types of sensors such as temperature sensors, humidity sensors, chronometers, heat flow sensors capable of measuring heat and/or heat flow, motion sensors, pH sensors, location detectors, GPS sensors, MFC sensors. In the illustrative embodiment of FIG. 10A, a single sensor 1035 is positioned on the inside top surface of the cap 1025. Smart cap system 1000 also includes a transmitter 1045 adapted to transmit measurement data to a communication network or to another device. In another embodiment, smart cap system 1000 may also include a receiver. Smart cap system 1000 may also include other components such as a processing device, a memory, etc. Smart cap system 1000 includes a radio frequency identification (RFID) device 1046.

Figure 10B:
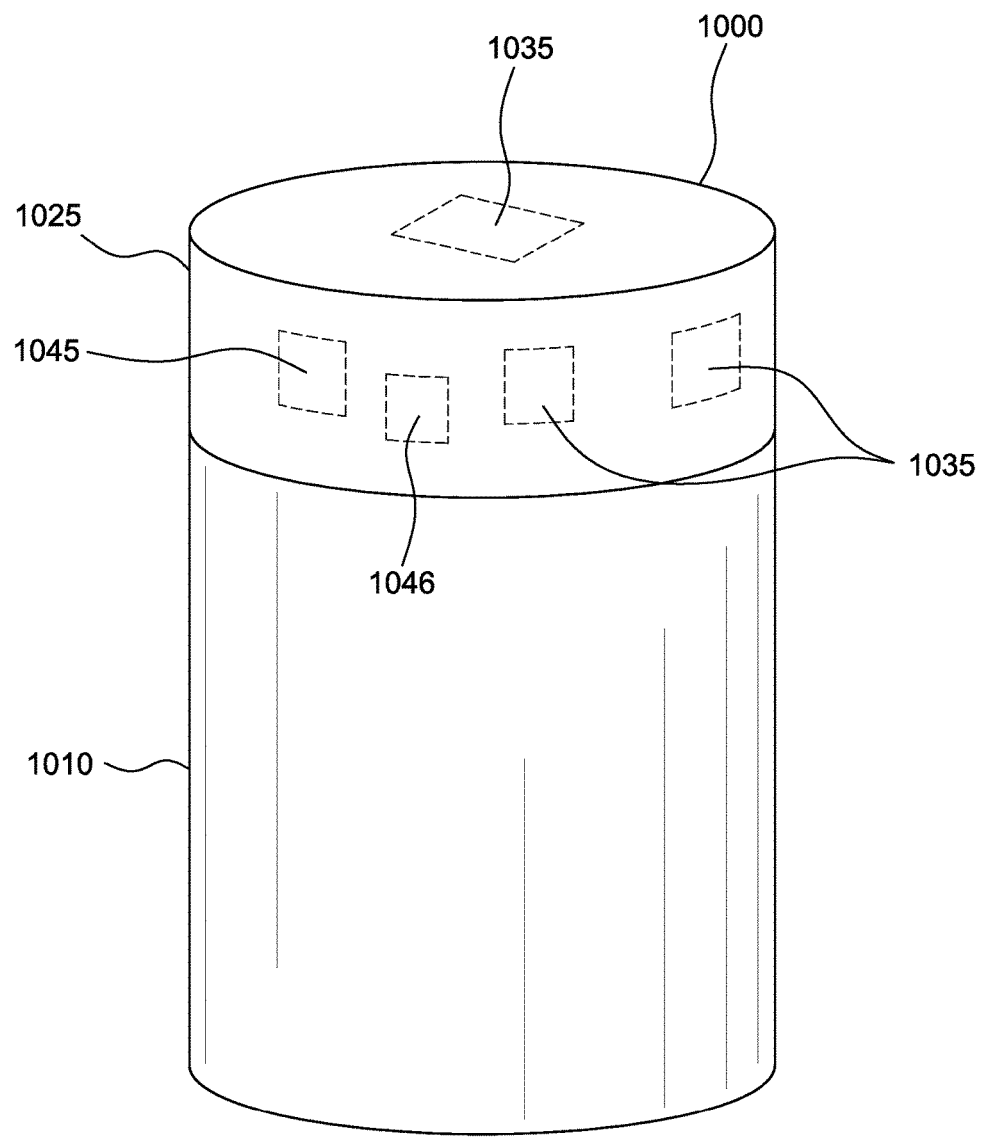
FIG. 10B shows a smart cap system fitted onto a test cylinder in accordance with an embodiment.

In accordance with an embodiment, smart cap system 1000 is placed on a test cylinder 1010. Test cylinder 1010 has a body 1084 having a first outer diameter and a top rim 1086 having a second outer diameter that is smaller than the first outer diameter of body 1084. Cap 1025 of smart cap system 1000 is adapted to fit onto top rim 1086; however, cap 1025 has an outer diameter equal to or substantially equal to the first outer diameter of the body 1084 of cylinder 1010. Accordingly, smart cap system 1000 may be fitted onto test cylinder 1010, as shown in FIG. 10B.

Figure 11A:
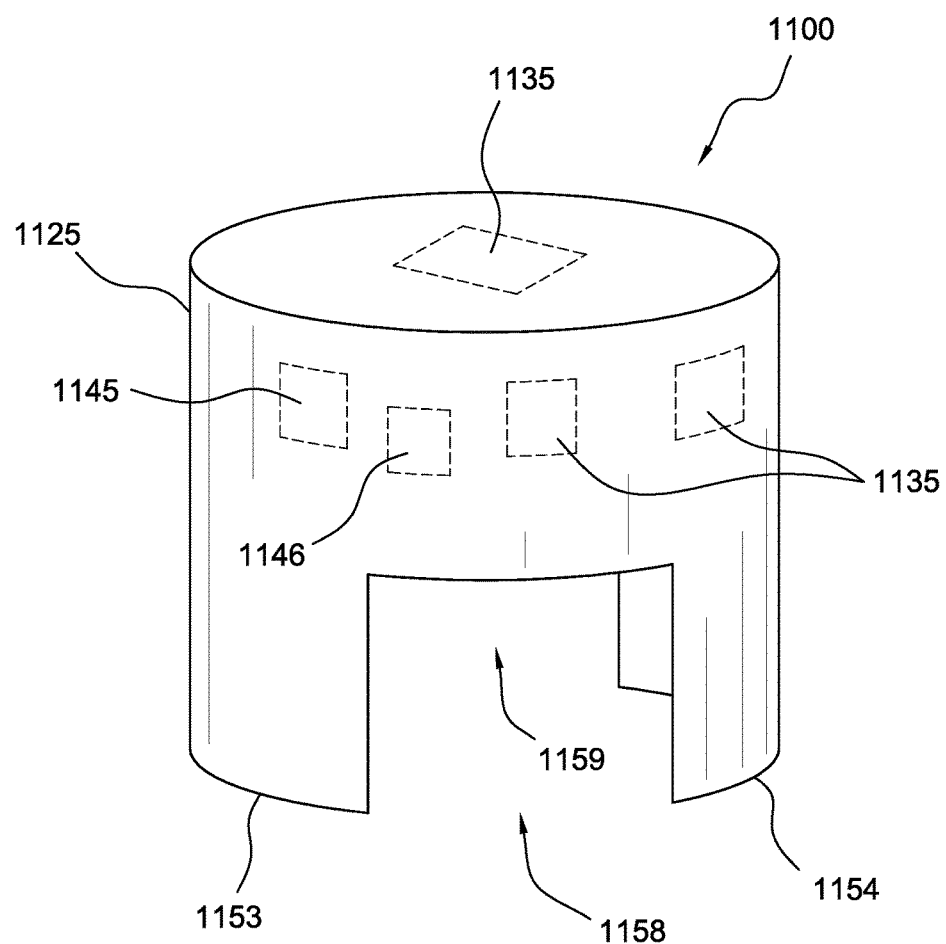
FIG. 11A shows a smart cap system in accordance with another embodiment.

FIG. 11A shows a smart cap system 1100 in accordance with another embodiment. Smart cap system 1100 includes a cap 1125, and one or more sensors 1135, which may include various types of sensors such as temperature sensors, humidity sensors, chronometers, heat flow sensors capable of measuring heat and/or heat flow, motion sensors, pH sensors, location detectors, GPS sensors, MFC sensors. In the illustrative embodiment of FIG. 10A, a single sensor 1135 is positioned on the inside top surface of the cap 1125. Smart cap system 1100 also includes a transmitter 1145 adapted to transmit measurement data to a communication network or to another device. In another embodiment, smart cap system 1100 may also include a receiver. Smart cap system 1100 may also include other components such as a processing device, a memory, etc. Smart cap system 1100 includes a radio frequency identification (RFID) device 1146.

Figure 11B:
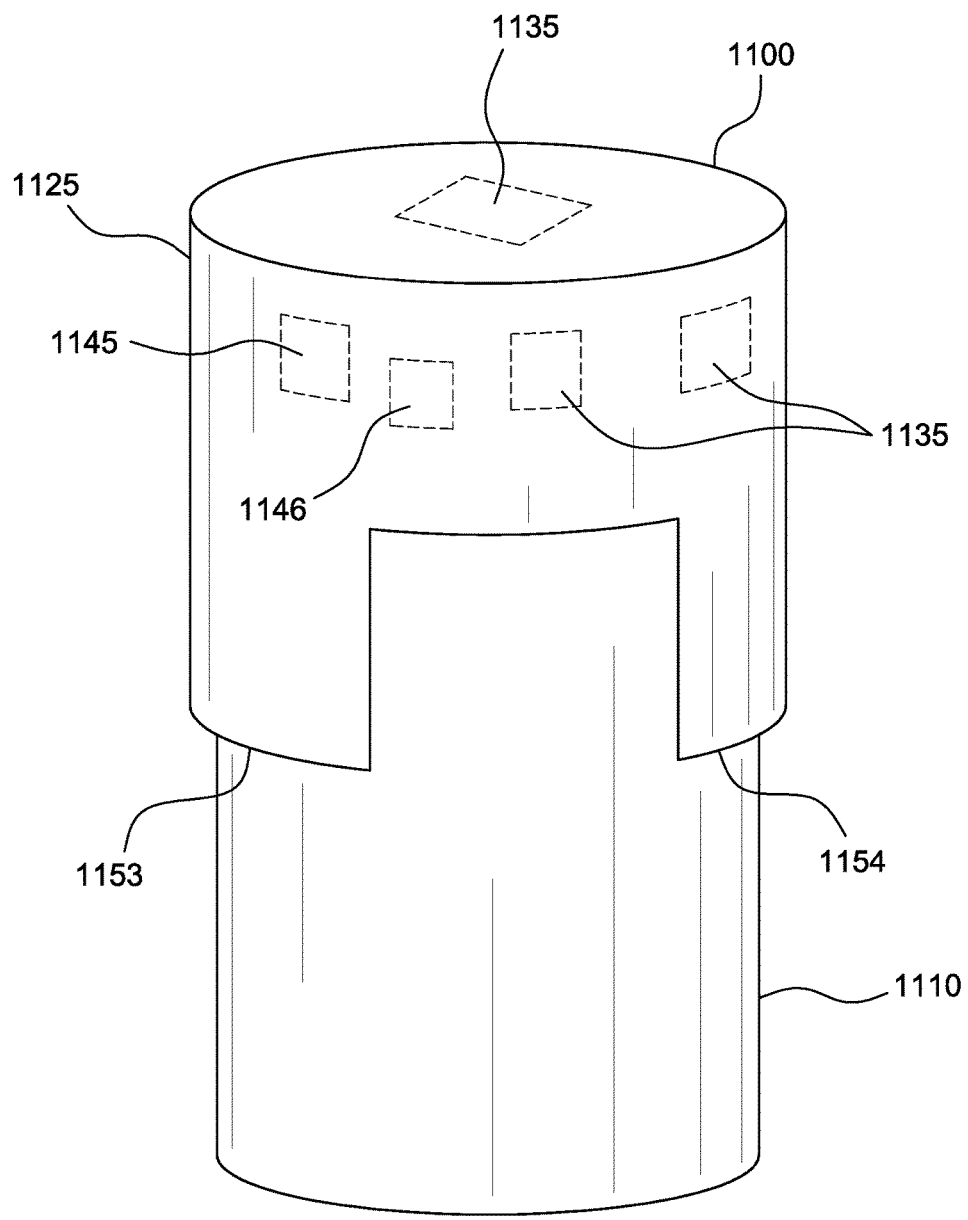
FIG. 11B shows a smart cap system fitted onto a test cylinder in accordance with an embodiment.

Cap 1125 includes two projecting portions 1153 and 1154 which project downward (away from the top surface of the cap) on opposite sides of the cap. Projecting portions 1153, 1154 define gaps 1158, 1159 in cap 1125. In accordance with an embodiment, smart cap system 1100 is placed on a test cylinder 1110, as shown in FIG. 11B. Advantageously, the projecting portions 1153, 1154 also extends the overlap of the cap over the cylinder and provides insulation for the concrete and cause it to self-heat due to hydration.

In other embodiments (in which the cap has a different shape), extending the overlap of the cap over the cylinder provides insulation for the concrete and cause it to self-heat due to hydration.

Figure 11C:
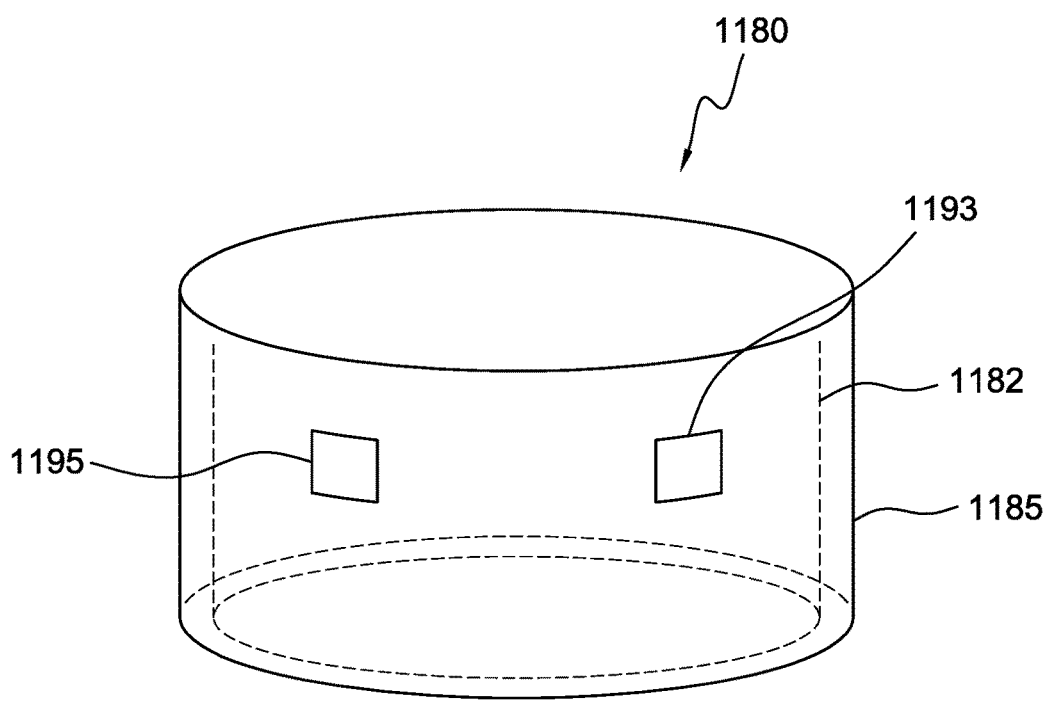
FIG. 11C shows a smart cap system in accordance with another embodiment.

FIG. 11C shows a smart cap system in accordance with another embodiment. Smart cap system 1180 includes a double-walled cap. The cap includes an inner wall 1182 and an outer wall 1185, and several sensors 1193, 1195. In various embodiments, a volume between the inner and outer walls may be filled with air, which may provide an insulating function, or with a selected type of insulation material. Advantageously, by using a double-walled construction with air insulation, or using another insulation method, the smart cap system is insulated (so that its temperature sensor measures the concrete temperature by being closely positioned to the cylinder surface).

In accordance with an embodiment, the cap of a smart cap system ends at the cylinder top in order to avoid self-heating of the concrete in the cylinder In various embodiments, the connection between the cap and the cylinder may constitute a seal. Advantageously, sealing moisture inside the cylinder and monitoring humidity facilitates efficient curing of the concrete.

Figure 12:
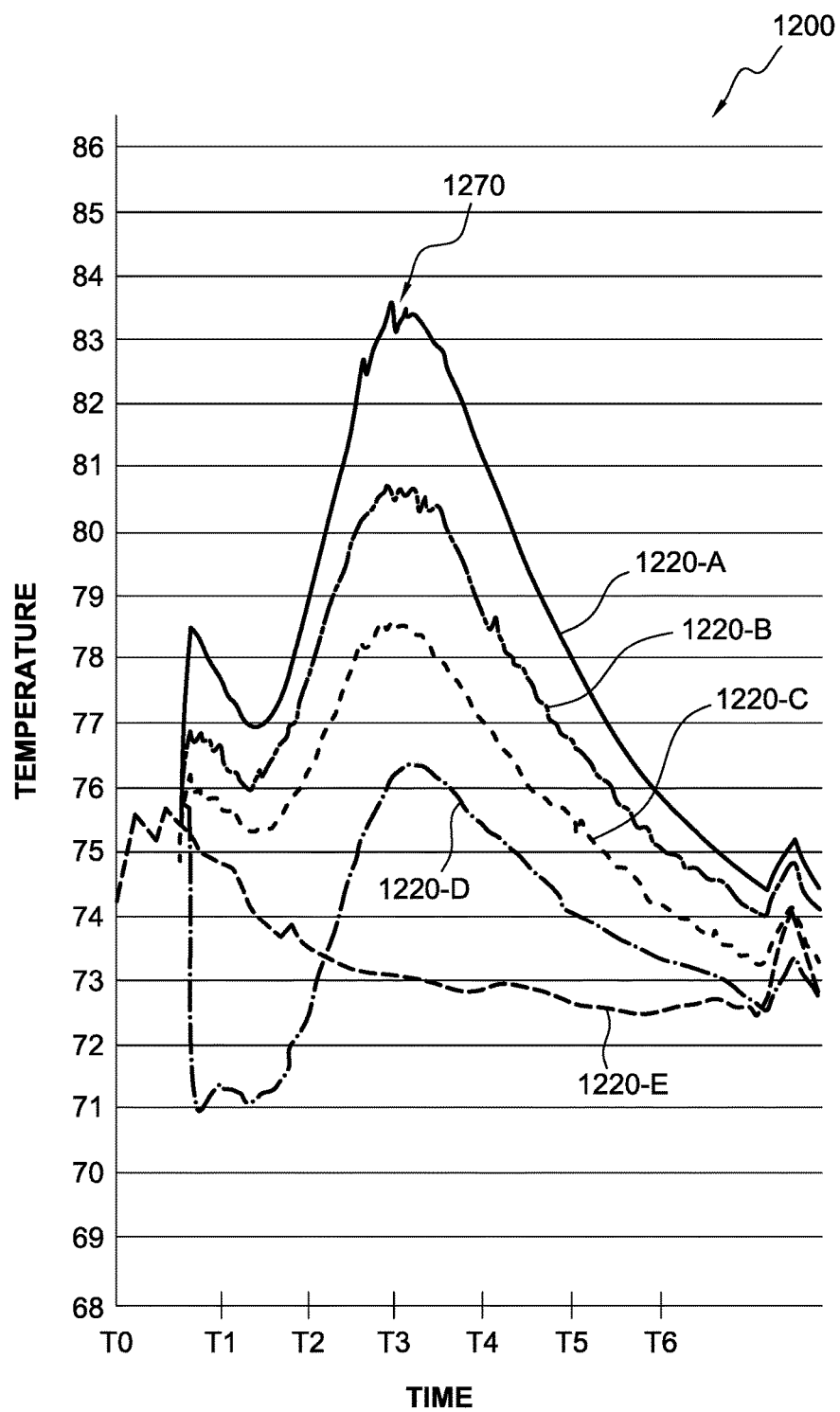
FIG. 12 includes a graph showing observed temperature measurements.

FIG. 12 includes a graph showing observed temperature over time measured after a concrete mixture has been poured into a test cylinder. Graph 1200 includes five sets of temperature measurements 1220-A, 1220-B, 1220-C, 1220-D, and 1220-E obtained using a smart cap system. The observed measurements show that after the concrete mixture is poured into the test cylinder, temperature begins at an initial temperature, rises from an initial temperature to a maximum (such as point 1270), and then gradually decreases. Advantageously, knowledge of the temperature profile associated with a particular specimen of concrete can be used to predict other characteristics of the concrete, such as strength, maturity, etc. Tests show that the initial temperature profile is sensitive to w/c ratio, mix design factors such as cement and water, chemical amounts and types, etc. For example, a smart cap system may detect additions of water made when a truck discharges concrete. Commonly, test cylinders are taken when the truck arrives at its initial discharge, and then the contractor may request that more water be added that weakens the concrete. Data obtained by a smart cap system may reflect the addition of additional water and may project loss of strength due to the added water. Advantageously, such data may be very helpful when site disputes relating to weakened concrete tests occur, for example. Such data may also provide a contractor information regarding when a batch of concrete is strong enough for form stripping.

In various embodiments, the method steps described herein, including the method steps described in FIG. 4, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 13:
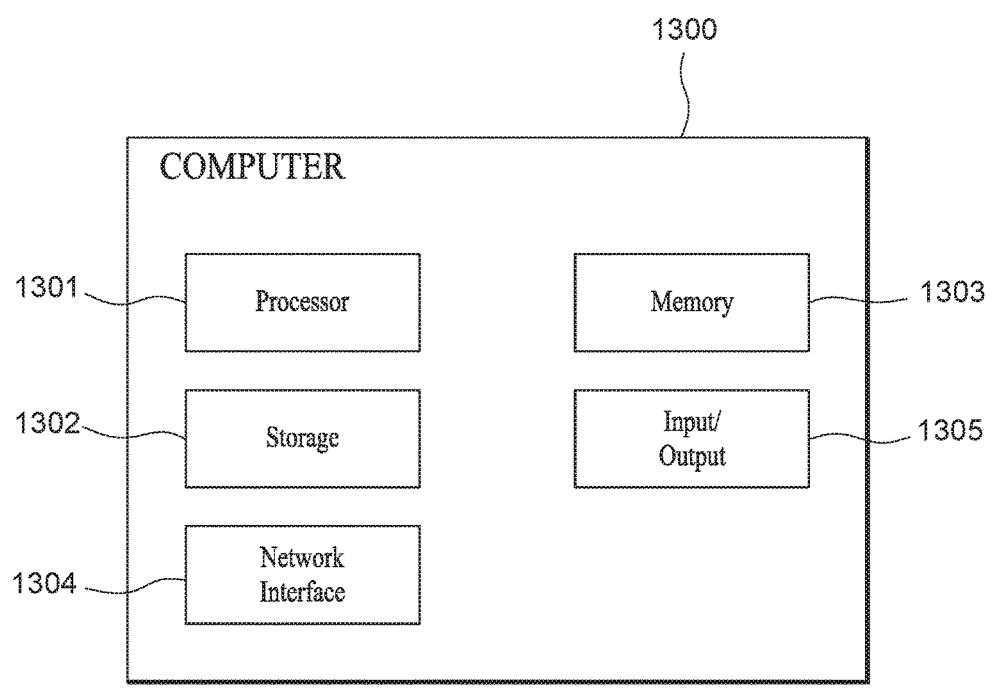
FIG. 13 shows an exemplary computer which may be used to implement certain embodiments.

A high-level block diagram of an exemplary computer that may be used to implement systems, apparatus and methods described herein is illustrated in FIG. 13. Computer 1300 includes a processor 1301 operatively coupled to a data storage device 1302 and a memory 1303. Processor 1301 controls the overall operation of computer 1300 by executing computer program instructions that define such operations. The computer program instructions may be stored in data storage device 1302, or other computer readable medium, and loaded into memory 1303 when execution of the computer program instructions is desired. Thus, the method steps of FIG. 4 can be defined by the computer program instructions stored in memory 1303 and/or data storage device 1302 and controlled by the processor 1301 executing the computer program instructions. For example, the computer program instructions can be implemented as computer executable code programmed by one skilled in the art to perform an algorithm defined by the method steps of FIG. 4. Accordingly, by executing the computer program instructions, the processor 1301 executes an algorithm defined by the method steps of FIG. 4. Computer 1300 also includes one or more network interfaces 1304 for communicating with other devices via a network. Computer 1300 also includes one or more input/output devices 1305 that enable user interaction with computer 1300 (e.g., display, keyboard, mouse, speakers, buttons, etc.).

Processor 1301 may include both general and special purpose microprocessors, and may be the sole processor or one of multiple processors of computer 1300. Processor 1301 may include one or more central processing units (CPUs), for example. Processor 1301, data storage device 1302, and/or memory 1303 may include, be supplemented by, or incorporated in, one or more application-specific integrated circuits (ASICs) and/or one or more field programmable gate arrays (FPGAs).

Data storage device 1302 and memory 1303 each include a tangible non-transitory computer readable storage medium. Data storage device 1302, and memory 1303, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1305 may include peripherals, such as a printer, scanner, display screen, etc. For example, input/output devices 1305 may include a display device such as a cathode ray tube (CRT) or liquid crystal display (LCD)

monitor for displaying information to the user, a keyboard, and a pointing device such as a mouse or a trackball by which the user can provide input to computer 1300.

Any or all of the systems and apparatus discussed herein, including smart cap 200, communication device 245, smart cap 500, smart cap 800, smart cap 1000, smart cap 1100, data manager 335, storage 360, network storage 960, data manager 935, local gateway 924, local storage 927, user device 390, user device 990, and components thereof, may be implemented using a computer such as computer 1300.

One skilled in the art will recognize that an implementation of an actual computer or computer system may have other structures and may contain other components as well, and that FIG. 13 is a high level representation of some of the components of such a computer for illustrative purposes.

It has been observed that high levels of humidity may develop within a test cylinder containing a concrete mixture. Under some conditions, high levels of humidity can damage electronic circuits, such as the electronic circuits present in a sensor device. Therefore, there is a need for an improved sensor holding apparatus that is capable of holding a sensor device within a test cylinder, in order to allow the sensor to obtain measurements relating to the concrete mixture, and is also capable of protecting the sensor device from excessively high levels of humidity.

Figure 14:
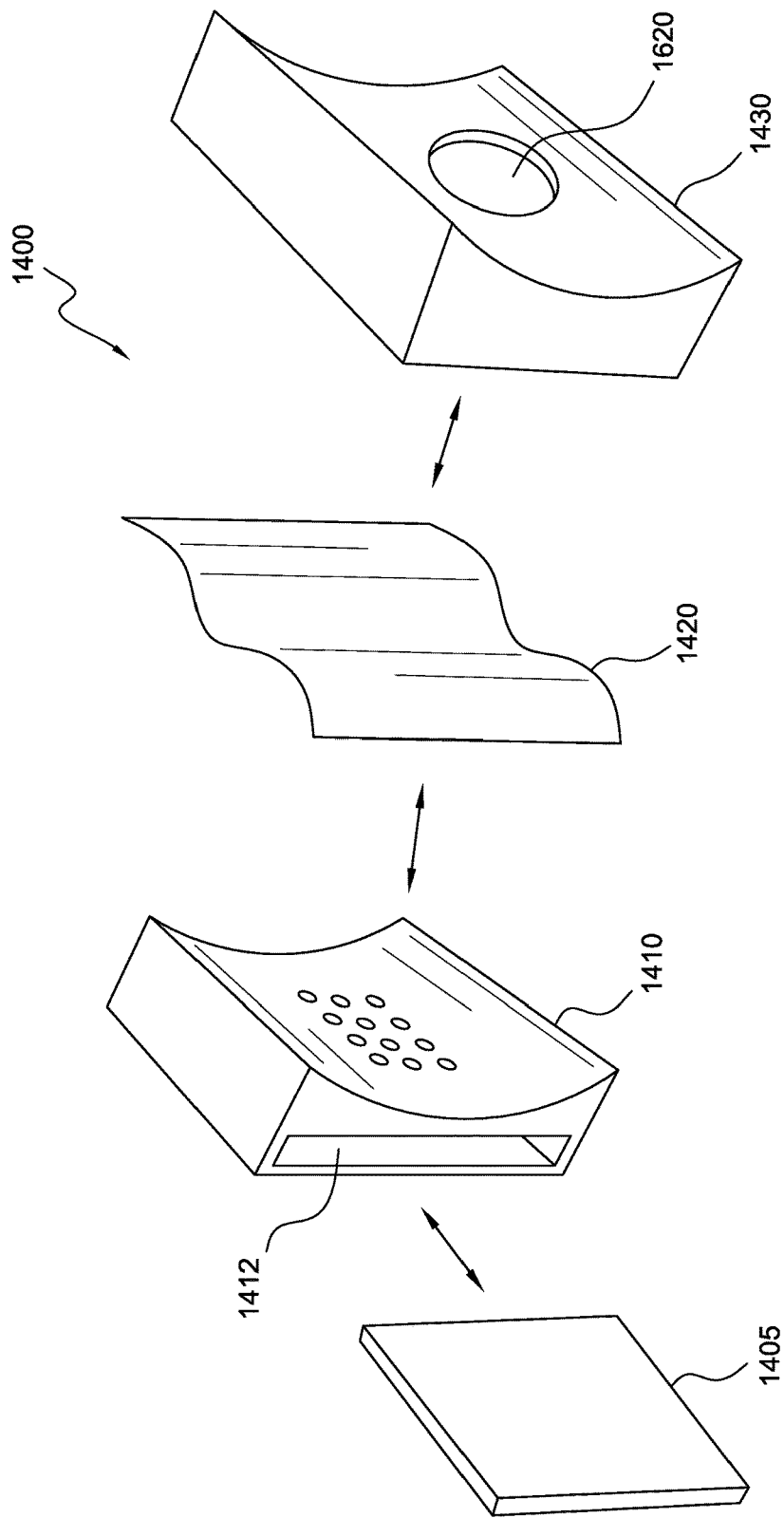
FIG. 14 shows components of a sensor holder system in accordance with an embodiment.

FIG. 14 shows components of a sensor holder system in accordance with an embodiment. Sensor holder system 1400 includes a sensor device 1405, a sensor enclosure 1410, a fabric membrane 1420, and a sensor holder cover 1430.

Sensor device 1405 includes one or more sensors adapted to obtain measurements relating to one or more selected characteristics of a concrete mixture. Sensor device 1405 is adapted to fit into an opening 1412 of sensor enclosure 1410. Sensor enclosure 1410 includes opening 1412 that is adapted to receive sensor device 1405. Sensor enclosure 1410 contains a volume that is adapted to hold and provide protection for sensor device 1405.

Fabric membrane 1420 is a waterproof, breathable fabric membrane. Fabric membrane 1420 may comprise a Gor-Tex material, for example, or a similar material. Fabric membrane 1420 may be 100% waterproof or may be partially waterproof. Fabric membrane 1420 protects sensor device 1405 from excessive humidity within a test cylinder containing a concrete mixture. Fabric membrane 1420 may permit a lower level of water vapor/humidity to pass through.

Sensor holder cover 1430 is adapted to receive and hold the assembly including sensor enclosure 1410 and fabric membrane 1420.

For example, sensor device 1405 may include a temperature sensor, a humidity sensor, a salinity sensor, a pH sensor, an inductance sensor, an impedance or resistivity sensor, a sonic sensor, a pressure sensor, a conductivity sensor a chronometer, a heat flow sensor, a motion sensor, an accelerometer, a location detector, an elevation sensor, a GPS sensor, a MFC sensor, or other types of sensor. Sensor device 1405 may include more than one type of sensor. One example of the temperature sensor is a miniature-sized temperature logger "SMARTBUTTON" (ACR SYSTEMS INC.). In one embodiment, a salinity sensor may include a chloride ion electrode, for example.

Sensor device 1405 may also include a wireless transmitter adapted to transmit measurement data. Sensor device 1405 may also include a receiver device adapted to receive commands and/or data.

Figure 15A:
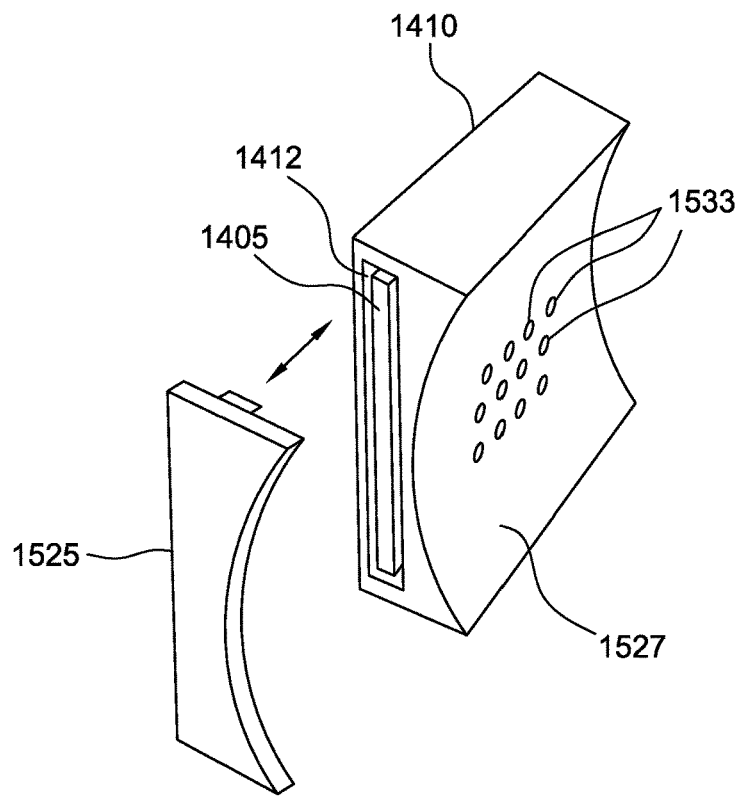
FIGS. 15A-15B show a sensor enclosure in accordance with an embodiment.
Figure 15B:
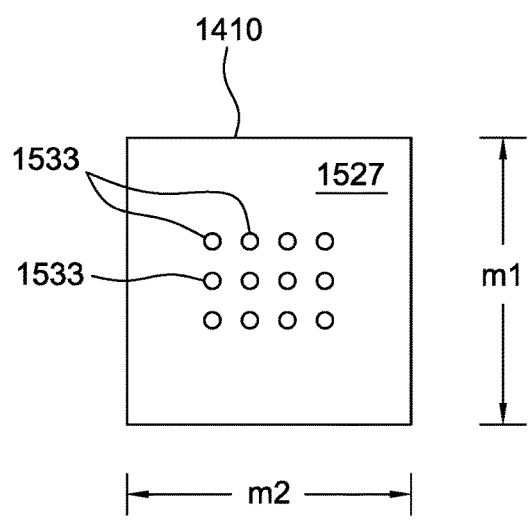

FIGS. 15A-15B show sensor enclosure 1410 in accordance with an embodiment. A slot or volume inside sensor enclosure 1410 is accessible via opening 1412; the slot or volume is adapted to hold sensor device 1405. Sensor device 1405 is housed within sensor enclosure 1410. Sensor enclosure includes a curved face having a surface 1527 that includes a plurality of holes 1533. Holes 1533 allow air to pass into the inside of sensor enclosure to sensor device 1405. In the illustrative embodiment of FIG. 15A, a cover component 1525 may be coupled to sensor enclosure 1525 in order to cover opening 1412 and provide further protection for sensor device 1405. Cover component 1525 may cover the entire side of sensor enclosure 1410 that includes opening 1412, for example.

Sensor enclosure 1410 has a first width dimension m1, which may be between 1.5 and 2.0 inches, for example, more preferably 1.71 inches, and a second width dimension m2, which may be between 1.5 and 2.0 inches, for example, more preferably 1.72 inches.

Figure 16A:
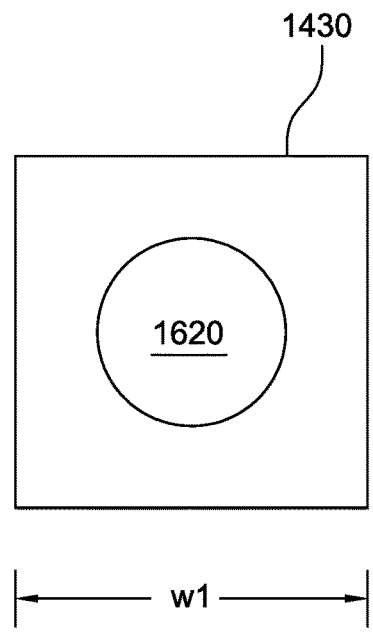
FIGS. 16A-16B show a sensor holder cover in accordance with an embodiment.
Figure 16B:
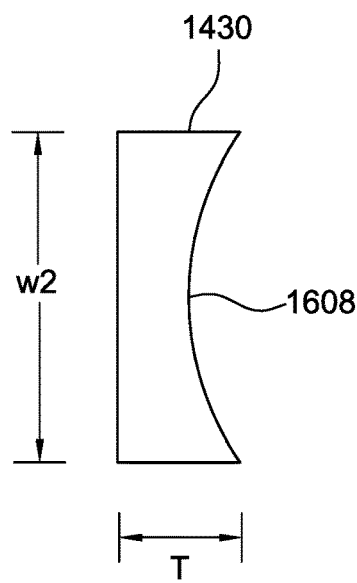

FIGS. 16A-16B show sensor holder cover 1430 in accordance with an embodiment. A curved side 1608 of sensor holder cover 1430 includes a central hole 1620. Sensor holder cover 1430 has first width dimension w1, which may be between 1.5 and 2.4 inches, for example, more preferably 2.01 inches. Sensor holder cover 1430 has a second width dimension w2, which may be between 1.5 and 2.0 inches, more preferably 1.84 inches. Sensor holder cover 1430 has a third width dimension T, which may be between 0.5 and 1.0 inches, for example, more preferably 0.68 inches.

Figure 17A:
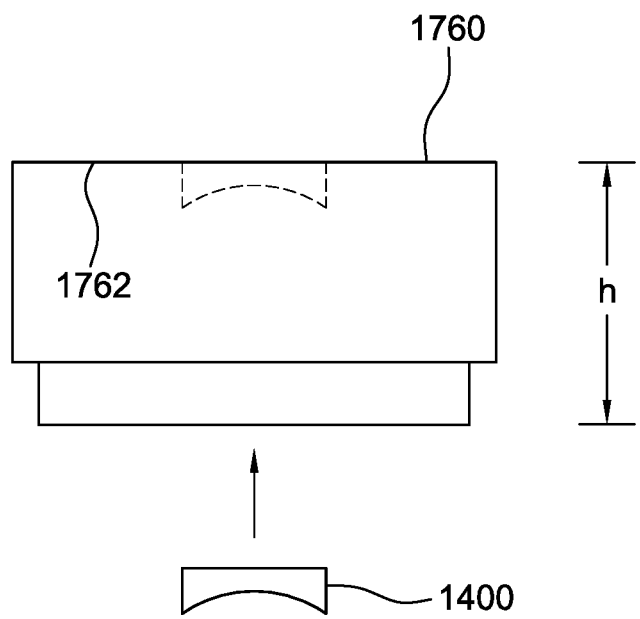
FIGS. 17A-17B show a smart cap system in accordance with another embodiment.
Figure 17B:
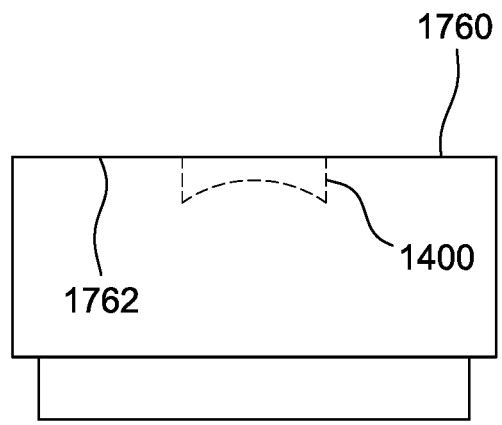

FIGS. 17A-B show a smart cap system in accordance with another embodiment. Sensor holder system 1400 may be attached to an internal surface of smart cap system 1760. For example, sensor holder system 1400 may be attached to an internal top surface 1762 of smart cap system 1760, as shown in FIGS. 17A-17B. In a manner similar to that described herein, smart cap system 1760 may then be placed on a cylinder 1770 containing a specimen of a concrete mixture 1785.

Figure 17C:
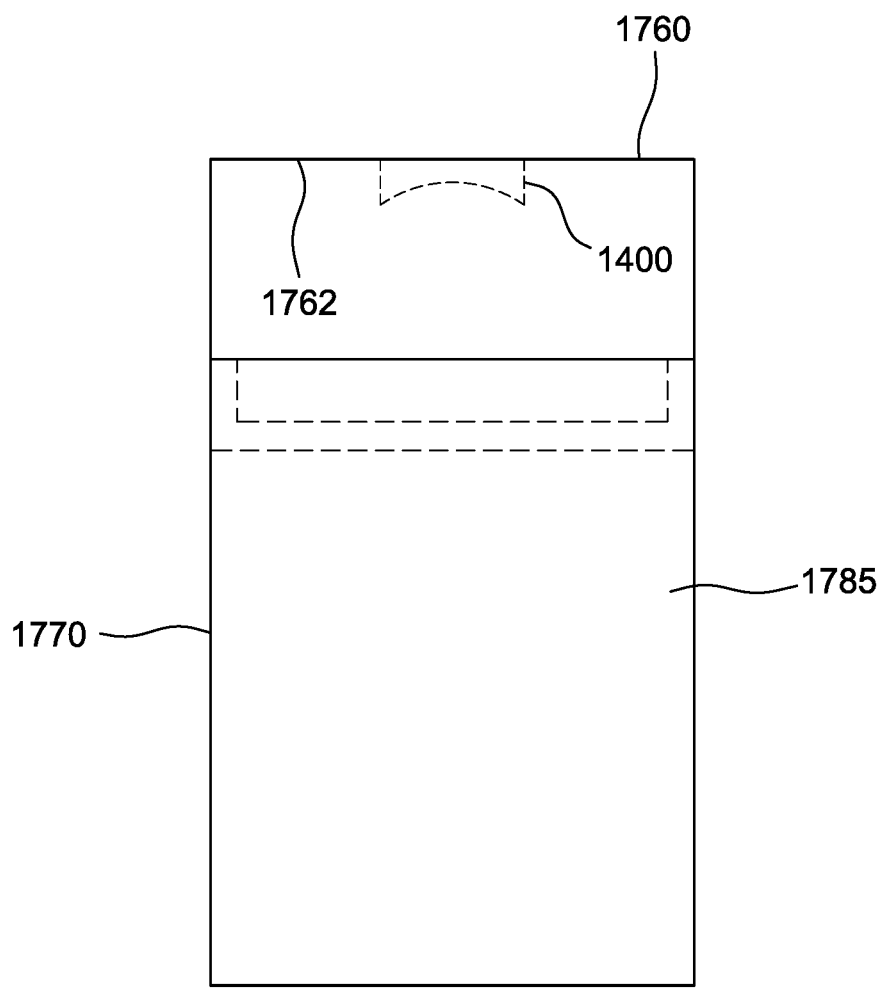
FIG. 17C shows a smart cap system placed on a test cylinder containing a concrete mixture in accordance with an embodiment.

FIG. 17C shows smart cap system 1760 placed on a test cylinder 1770 containing a concrete mixture 1785 in accordance with an embodiment. Sensor holder system 1400 is disposed on internal surface 1762 of smart cap system 1760, In accordance with systems and methods described herein, sensor 1405 may obtain measurements of one or more characteristics of concrete mixture 1785.

Advantageously, fabric membrane 1420, and more generally the structure of sensor holder system 1400, protect sensor device 1405 from excessively high levels of humidity that may develop within cylinder 1770. In particular, any air or gases, including any water vapor, inside test cylinder 1770 are restricted from reaching sensor device 1405 by hole 1620 of sensor holder cover 1430, fabric membrane 1420, and holes 1533 of sensor enclosure 1410. If fabric membrane 1420 is less than 100% waterproof, a reduced level of water vapor may reach sensor device 1405 under some conditions.

Figure 18:
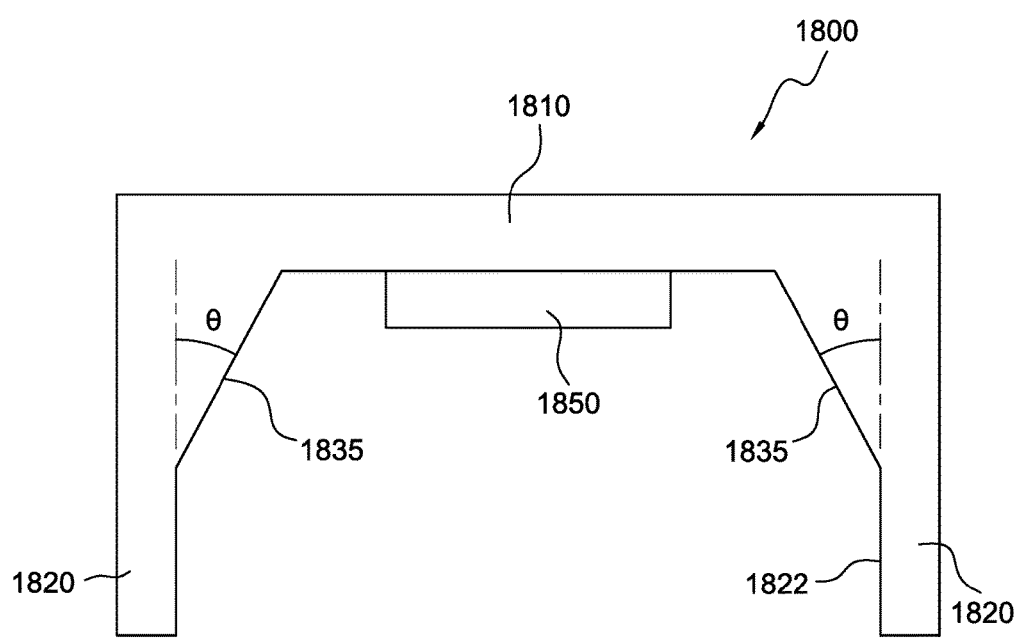
FIG. 18 shows a cross-section of a smart cap system in accordance with an embodiment.

FIG. 18 shows a smart cap system in accordance with another embodiment. Smart cap system 1800 includes a top portion 1810 and a round side portion 1820, which is adapted to fit over a standard test cylinder. A sensor device 1850 is attached to the interior surface of top portion 1810.

In the interior of the cap, top portion 1810 and side portion 1820 do not form a right angle. Instead, an angled portion 1835 joins top portion 1810 and side portion 1820. Angled portion 1835 forms an angle θ relative to an interior surface 1822 of side portion 1820. In one embodiment, angle θ is thirty (30) degrees. In other embodiments, angle θ is between 20 degrees and 40 degrees. The surface of angled portion 1835 is smooth (to reduce friction). In another embodiment, the surface of angled portion is rough (to generate friction).

Figure 19:
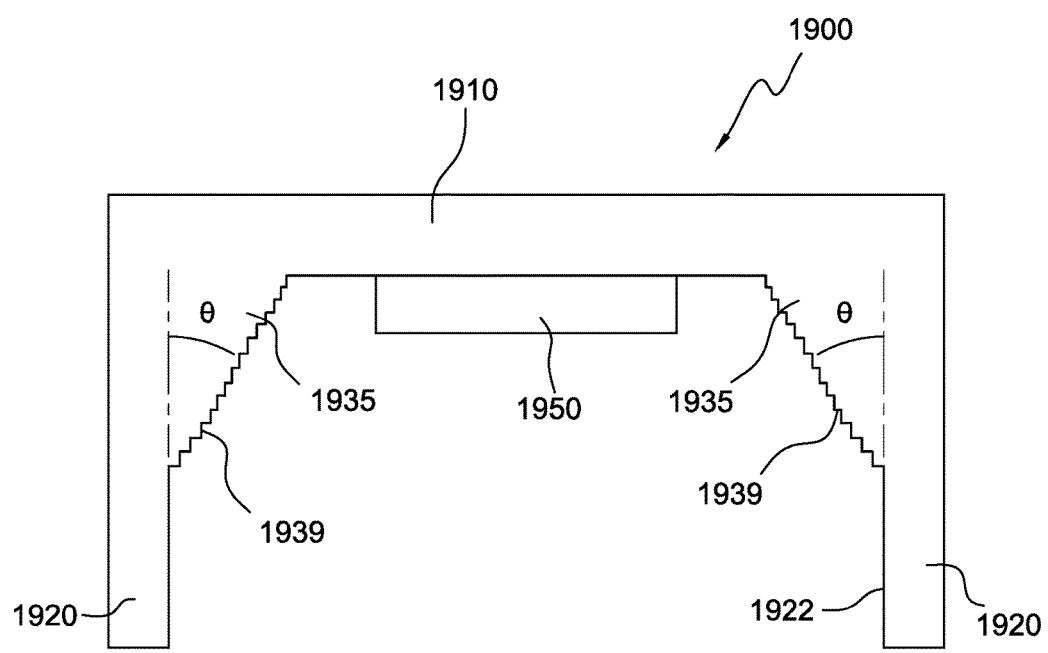
FIG. 19 shows a cross-section of a smart cap system in accordance with an embodiment.

FIG. 19 shows a smart cap system in accordance with another embodiment. Smart cap system 1900 includes a top portion 1910 and a round side portion 1920, which is adapted to fit over a standard test cylinder. A sensor device 1950 is attached to the interior surface of top portion 1910.

In the interior of the cap, an angled portion 1935 joins top portion 1910 and side portion 1920. Angled portion 1935 forms an angle θ relative to an interior surface 1922 of side portion 1920. In one embodiment, angle θ is thirty (30) degrees. In other embodiments, angle θ is between 20 degrees and 40 degrees. A series of steps or ridges 1939 cover the surface of angled portion 1935.

Figure 20:
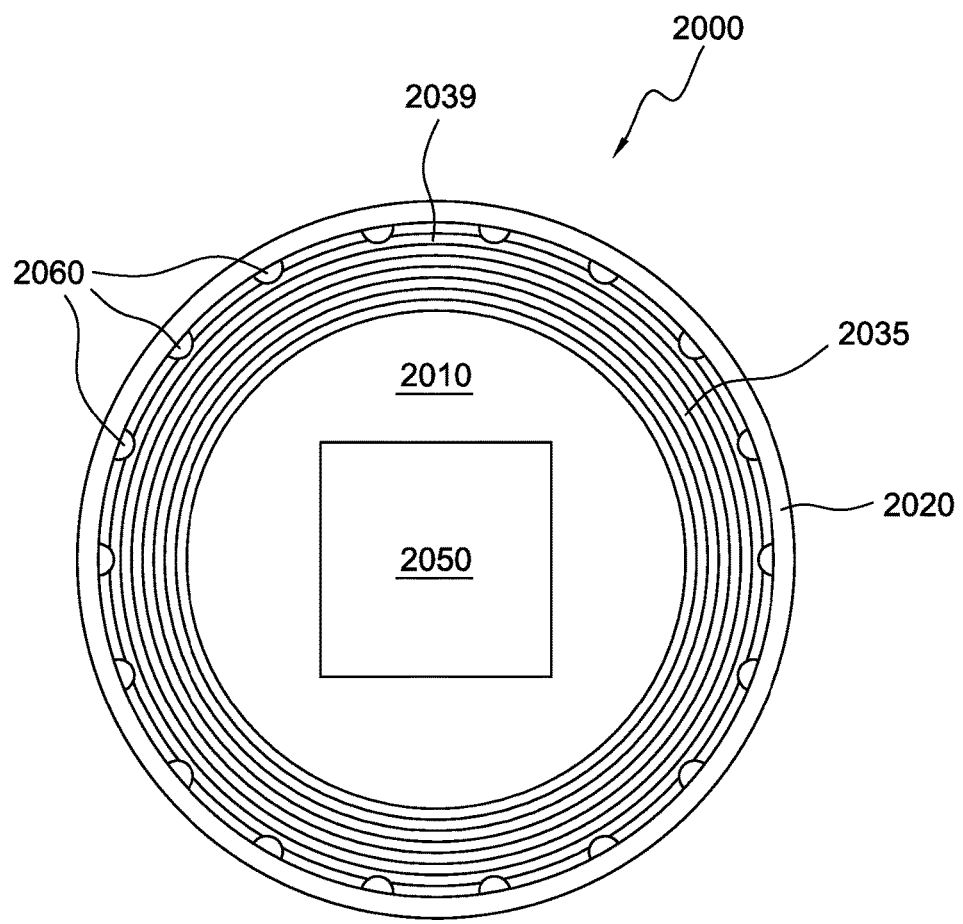
FIG. 20 shows a view of an interior surface of a smart cap system in accordance with an embodiment.

FIG. 20 shows a view of the interior surfaces of a smart cap system in accordance with an embodiment. Smart cap system 2000 includes a top portion 2010 and a round side portion 2020. A sensor device 2050 is attached to top portion 2010. Angled portion 2035 joins top portion 2010 and side portion 2020. The surface of angled portion 2035 includes ridges 2039. A plurality of spacers 2060 are disposed on the interior surface of side portion 2020. Spacers 2060 may be regularly or irregularly spaced on the interior surface of side portion 2020. Spacers 2060 may have a radial width of between 1 and 5 millimeters, for example. Other widths may be used. Advantageously, spacers 2060 facilitate the placement of smart cap system 2000 onto a test cylinder and also facilitate the removal of smart cap system 2000 from the test cylinder.

Figure 21:
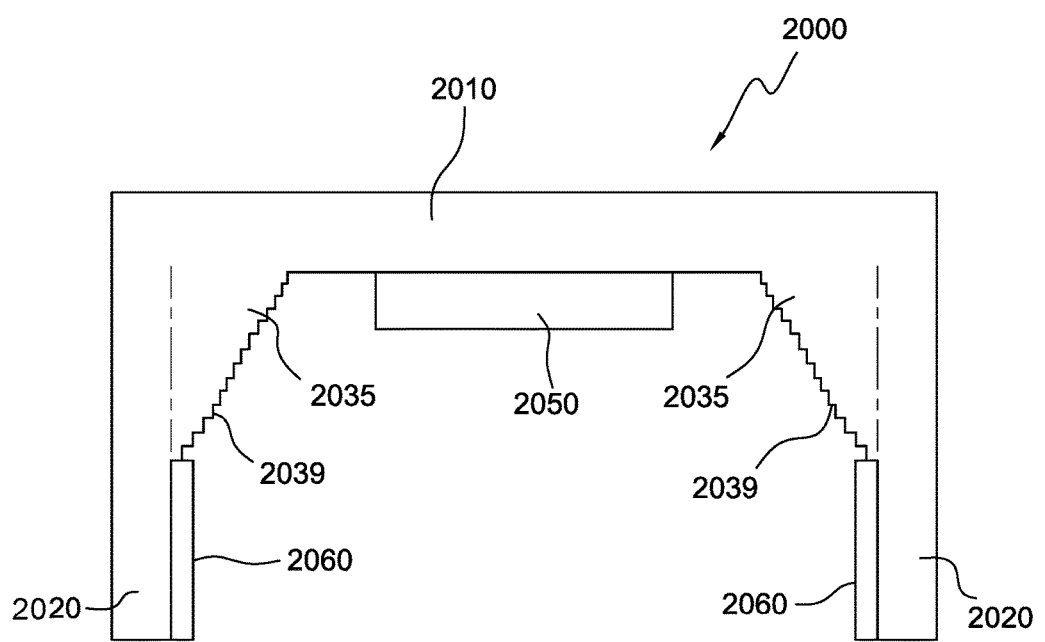
FIG. 21 shows a cross-section of a smart cap system in accordance with an embodiment.

FIG. 21 shows a cross section view of smart cap system 2000 of FIG. 20. Spacers 2060 extend from the bottom rim of side portion 2020 to angled portion 2035.

Figure 22:
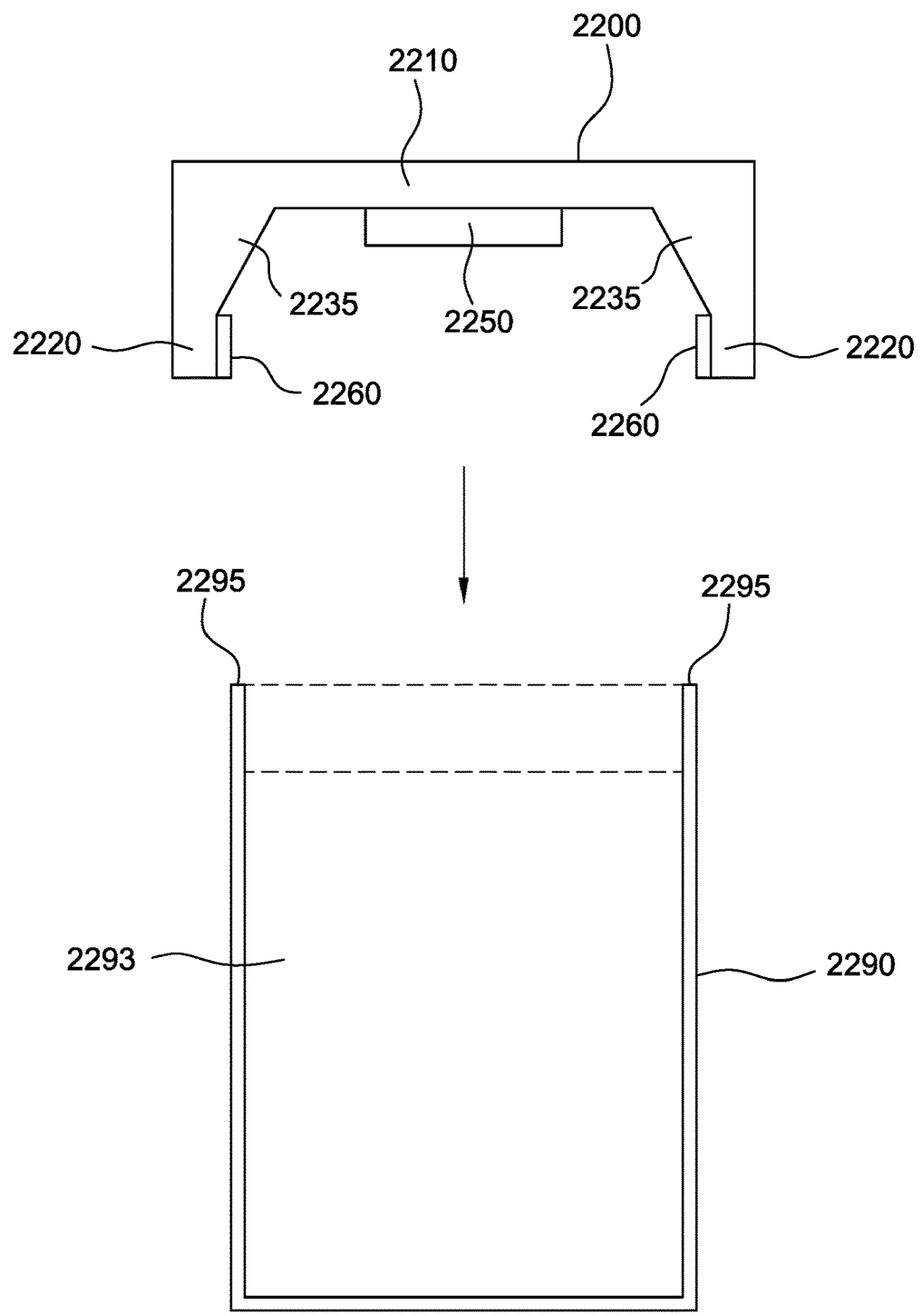
FIGS. 22-24 illustrate a method of placing a smart cap system onto a test cylinder in accordance with an embodiment.
Figure 23:
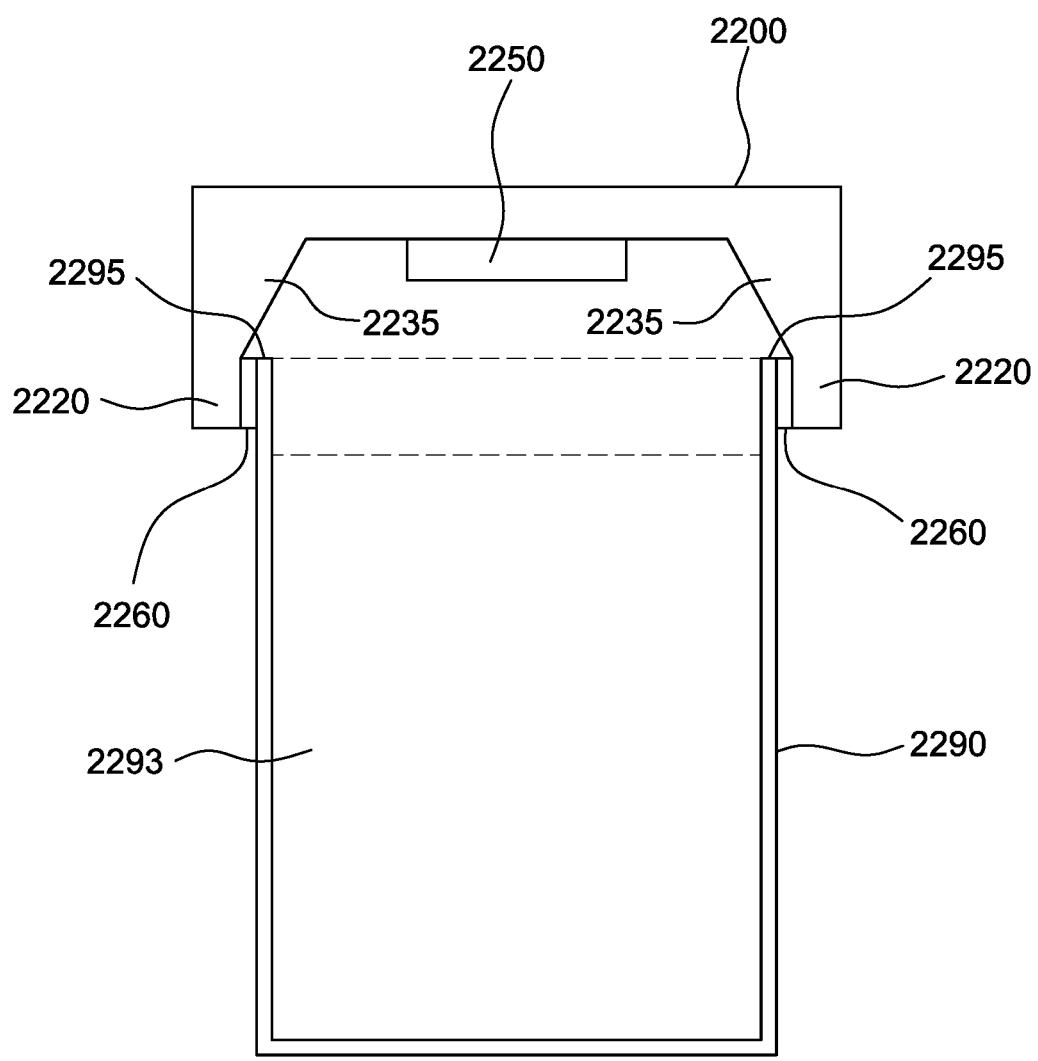
Figure 24:
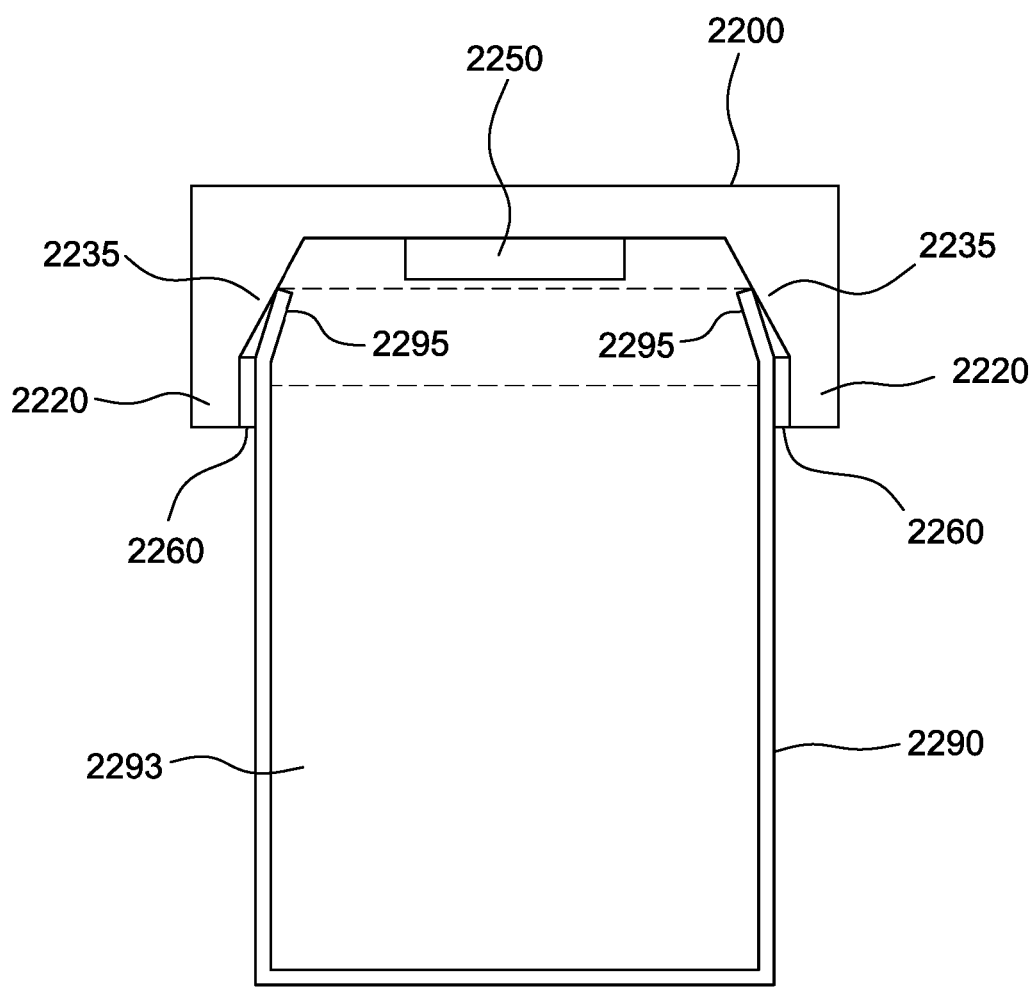

FIGS. 22-24 illustrate a method of placing a smart cap system onto a test cylinder in accordance with an embodiment. A smart cap system 2200 includes a top portion 2210, a side portion 2220, and an angled portion 2235. A sensor device 2250 is attached to an interior surface of top portion 2210. Spacer 2260 are disposed on an interior surface of side portion 2220.

Advantageously, when the cylinder onto which a smart cap system is placed is formed of a flexible material such as plastic, the angled portion of the smart cap system facilitates the formation of a seal between the cylinder and the interior surface of the smart cap system. This feature is illustrated in FIGS. 22-24.

Advantageously, a smart cap system such as those illustrated in FIGS. 18-21 provides a sealed environment, and therefore provides an environment with stable humidity. In such a sealed environment, the humidity inside the cylinder can remain at or near one hundred percent (100%) while the concrete dries. Because of the stable environment with one hundred percent humidity, the observed strength obtained when the concrete specimen is tested represents a valid and reliable measure of the concrete's strength.

Referring to FIG. 22, smart cap system 2200 is placed above a top rim 2295 of a test cylinder 2290, which holds a specimen of concrete 2293. Referring to FIG. 23, smart cap system 2200 is lowered to fit around top rim 2295 of test cylinder 2290. Smart cap cylinder is lowered until top rim 2295 of test cylinder 2290 reaches approximately the top end of spacers 2260. At this point, top rim 2295 of test cylinder 2290 is proximate angled portion 2235 of smart cap system 2200.

When smart cap system 2200 is pushed down further onto test cylinder 2290, angled portion 2235 of smart cap system comes into contact with top edge 2295 of test cylinder 2290. As smart cap system 2200 is pushed still further onto test cylinder 2290, the reduced radius of angled portion 2235 forces top rim 2295 of test cylinder 2290 to be squeezed. The reduced radius of angled portion 2235 creates a space having a radius smaller than the original radius of top rim of test cylinder 2290. At this stage, a small or moderate amount of pressure may need to be applied by a technician to push smart cap system onto test cylinder 2290. Because text cylinder 2290 is made from a flexible material, top rim 2295 bends in response to the applied force and the radius of top rim 2295 decreases, as shown in FIG. 24. A portion of the material of test cylinder 2290 proximate top rim 2295 may also be squeezed and bend to fit into the reduced spaced created by angled portion 2235.

Advantageously, after smart cap system 2200 is placed onto test cylinder 2290 in the manner described above and illustrated in FIGS. 22-24, the pressure created between top rim 2295 of test cylinder 2290 and the surface of angled portion 2235 creates a seal between smart cap system 2200 and test cylinder 2290.

It has been observed that when a test cylinder and smart cap system are used outdoors to test a specimen of concrete, the sensors within the smart cap system (and the smart cap system itself) may be affected (e.g., heated) by solar radiation and other environmental factors, thereby causing measurements to be unreliable or inaccurate. For example, if the test cylinder and smart cap system are in direct sunlight, the radiation from the direct sunlight may affect measurements obtained by sensors in or on the smart cap system. There is a need for systems and methods to ensure that measurements made by sensors in a smart cap system are reliable and accurate.

Figure 25:
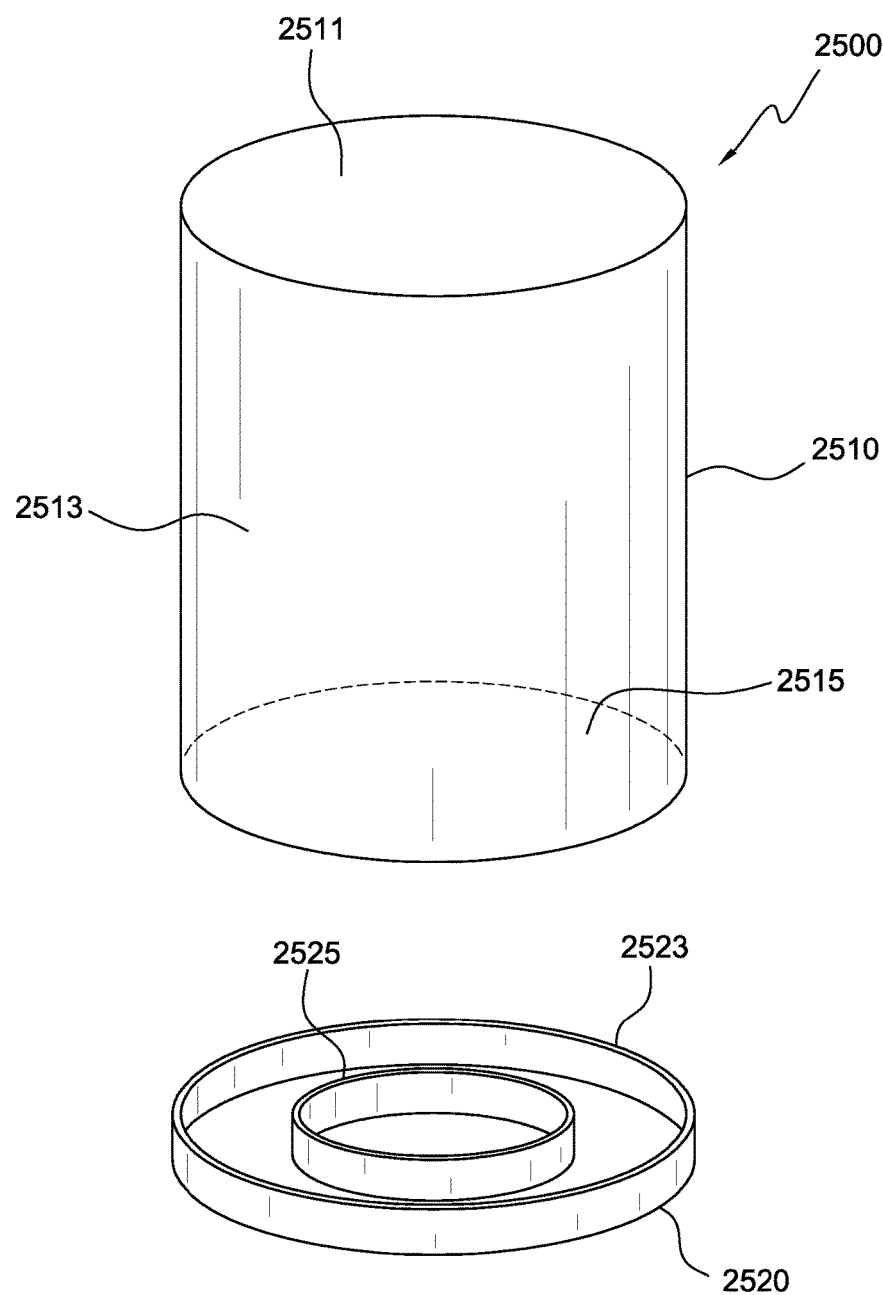
FIG. 25 shows a cylinder enclosure system in accordance with an embodiment.

FIG. 25 shows a cylinder enclosure system in accordance with an embodiment. Enclosure system 2500 includes a cover 2510 and a base 2520. Cover 2510 is a hollow cylinder having a closed top portion 2511 and a round side portion 2513, and an open bottom 2515. Base 2520 has an outer ring 2523 and an inner ring 2525. Cover 2510 is adapted to fit into outer ring 2523.

In one embodiment, cover 2510 and base 2520 are made from a plastic material. Other materials may be used.

Figure 26:
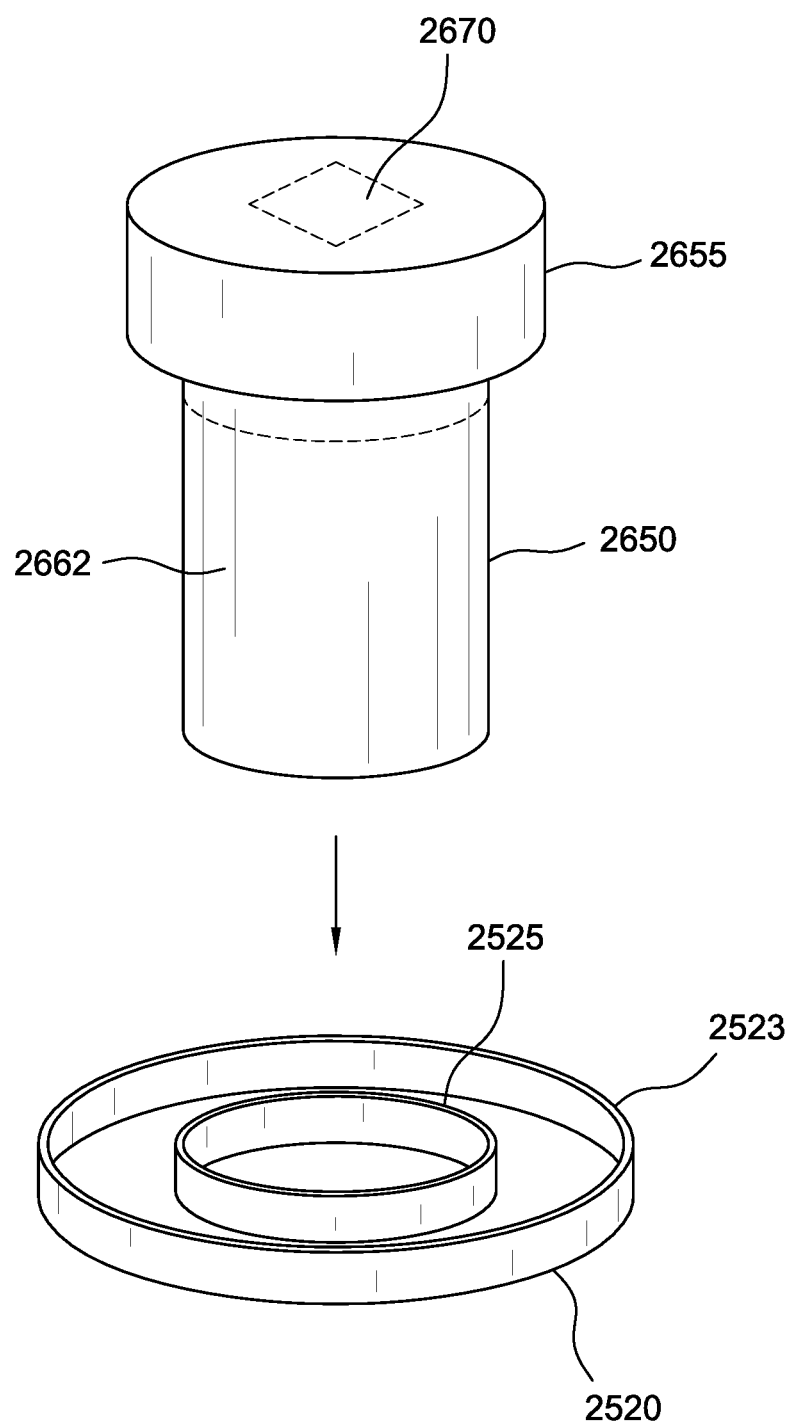
FIGS. 26-28 illustrate a method of placing a test cylinder in a cylinder enclosure system in accordance with an embodiment.

Referring to FIG. 26, inner ring 2525 of base 2520 is adapted to receive and hold a standard test cylinder. Therefore, in one embodiment, inner ring 2525 has a diameter of 4 inches and is adapted to receive a 4×8 test cylinder. In another embodiment, inner ring 2525 has a diameter of 6 inches and is adapted to receive a 6×12 test cylinder. Cover 2510 is adapted to cover and enclose a standard test cylinder. Accordingly, in one embodiment, cover 2510 is adapted to cover and enclose a 4×8 test cylinder. For example, cover 2510 may have dimensions of 6×12 inches, sufficient to cover a 4×8 test cylinder. Other dimensions may be used.

In another embodiment, cover 2510 is adapted to cover and enclose a 6×12 test cylinder. For example, cover 2510 may have dimensions of 9×18 inches, sufficient to cover a 6×12 test cylinder. Other dimensions may be used.

In one embodiment, the surface of cover 2500 includes a reflective material, such as foil, reflective paint, reflective sprayed material, etc. Cover 2500 may have a light-colored surface, such as white or silver.

Figure 27:
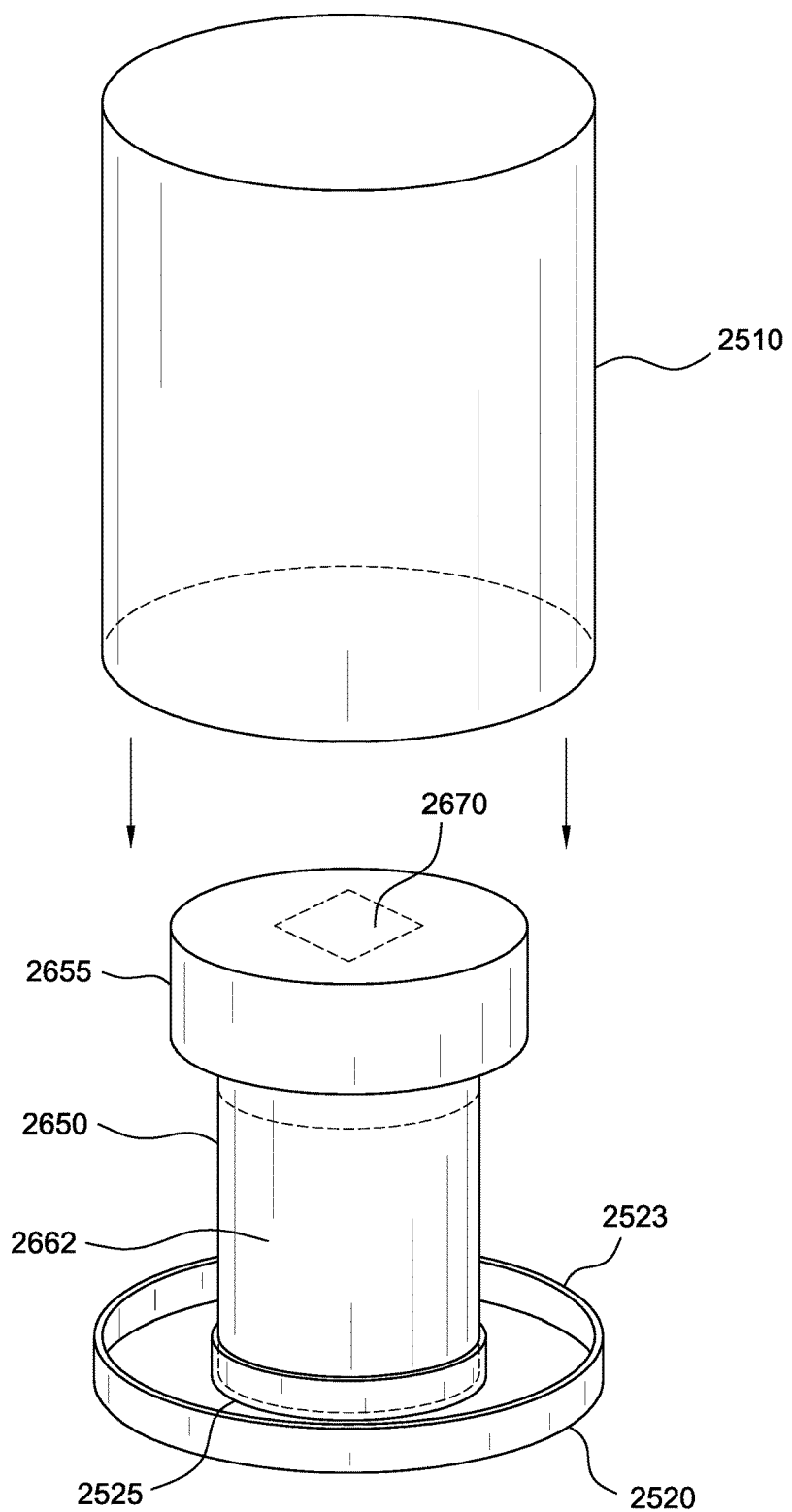
Figure 28:
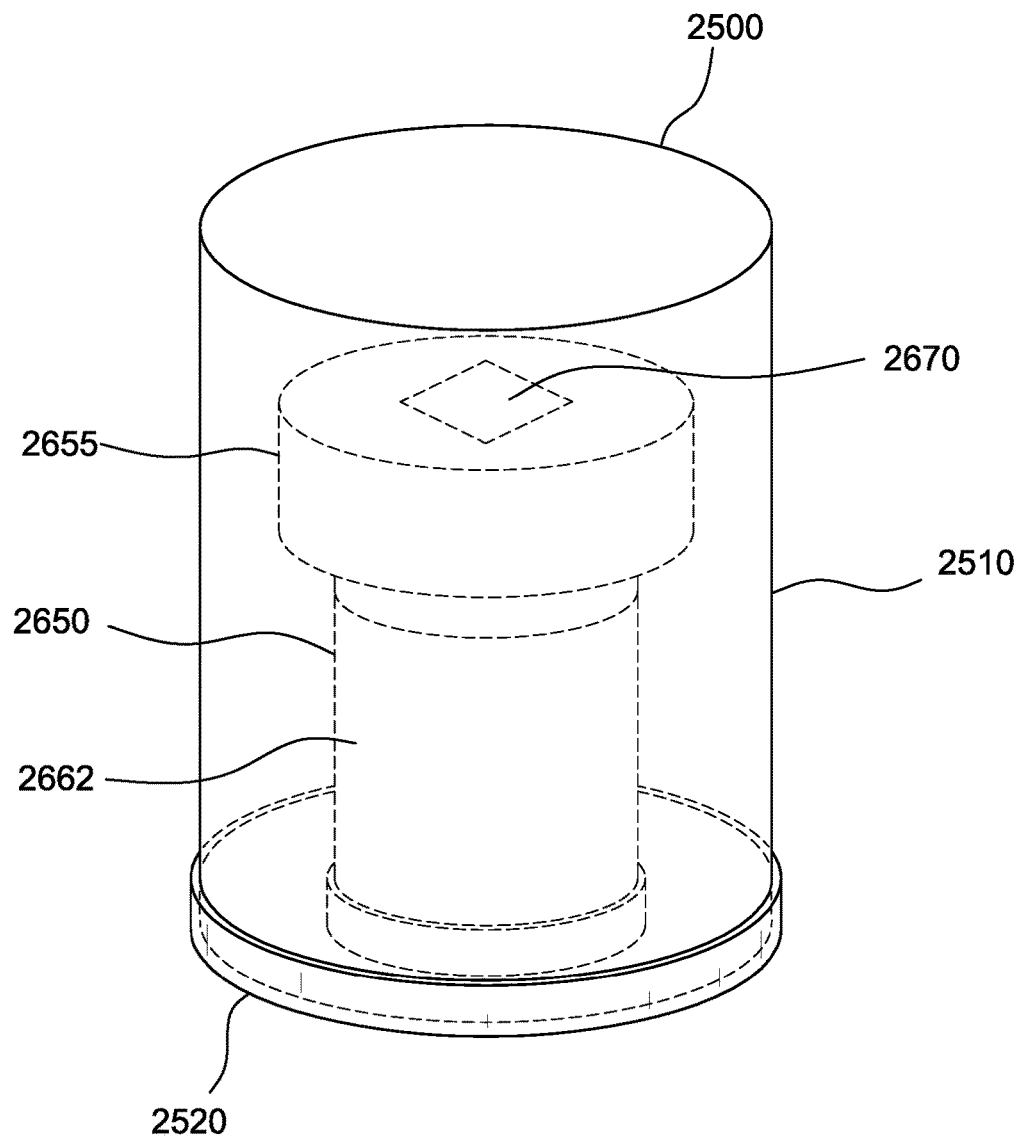

In one embodiment, a standard test cylinder is placed in cylinder enclosure system 2500. FIGS. 26-28 illustrate a method of placing a test cylinder into cylinder enclosure system 2500 in accordance with an embodiment. Referring to FIG. 26, a test cylinder 2650, including a cap 2655 and a sensor device 2670, and which holds a specimen of concrete 2662, is placed into inner ring 2525 of base 2520. Referring to FIG. 27, cover 2510 is placed over cylinder 2650 and cap 2655, and fits into outer ring 2523 of base 2520.

Referring to FIG. 28, test cylinder 2650 (and cap 2655) may remain within cylinder enclosure system 2500 as long as desired. For example, after a specimen of concrete is poured into test cylinder 2650 for the purpose of testing the concrete, the test cylinder may be placed into cylinder enclosure system 2500. The cylinder enclosure system 2500 (with the test cylinder 2650 inside) may then be placed outdoors for the duration of the test, for example. Advantageously, even in direct sunlight, cylinder enclosure system 2500 protects cylinder 2650, sensor 2670, and the specimen of concrete 2662, from the effects of solar radiation and other environmental factors.

Figure 29:
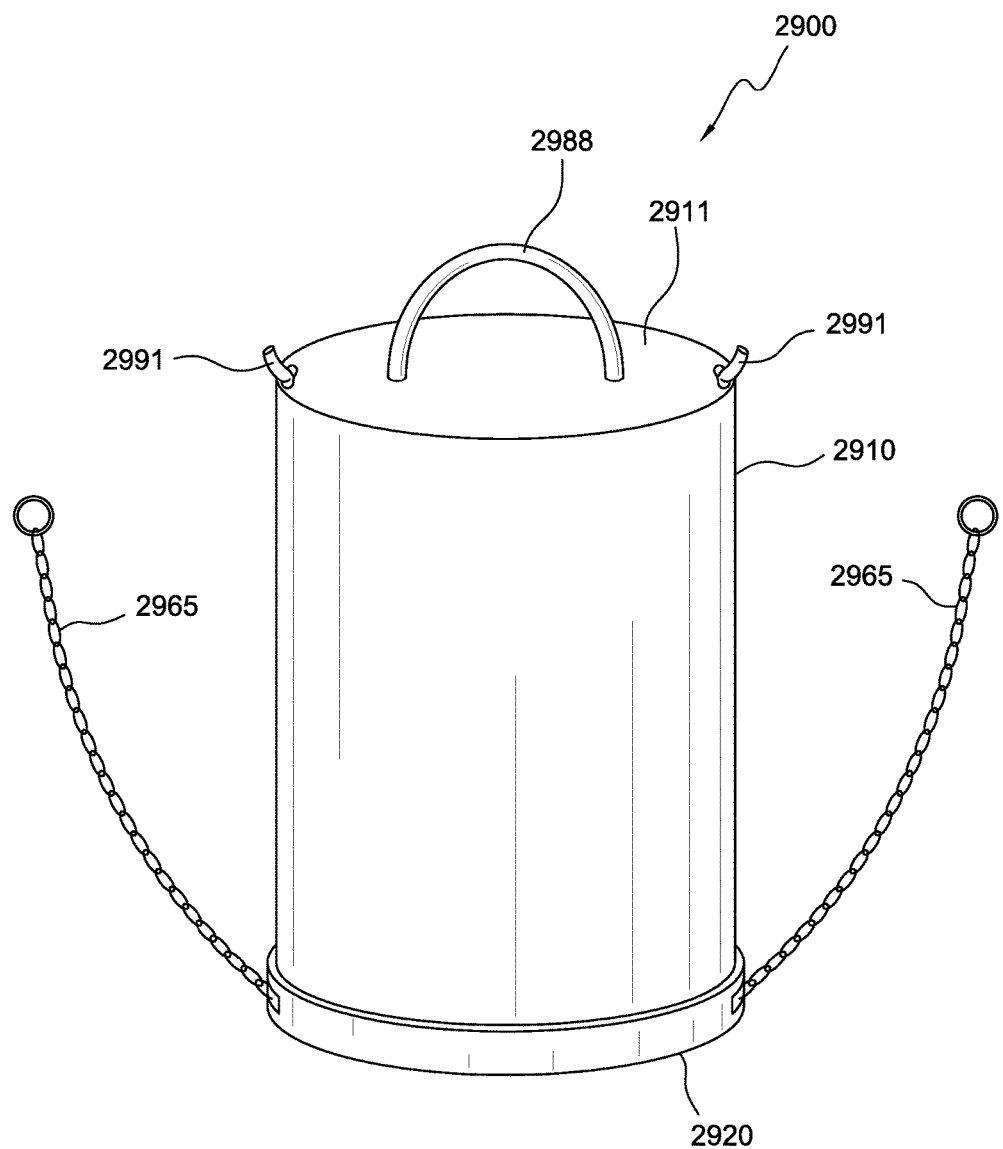
FIG. 29 shows a cylinder enclosure system in accordance with an embodiment.

FIG. 29 shows a cylinder enclosure system in accordance with another embodiment. System 2900 includes a cover 2910 and a base 2920. A handle 2988 is attached to a top surface 2911 of cover 2910. Two hooks 2991 are attached at the edges of top surface 2911 of cover 2910. Two chains 2965 are attached to base 2920.

Figure 30:
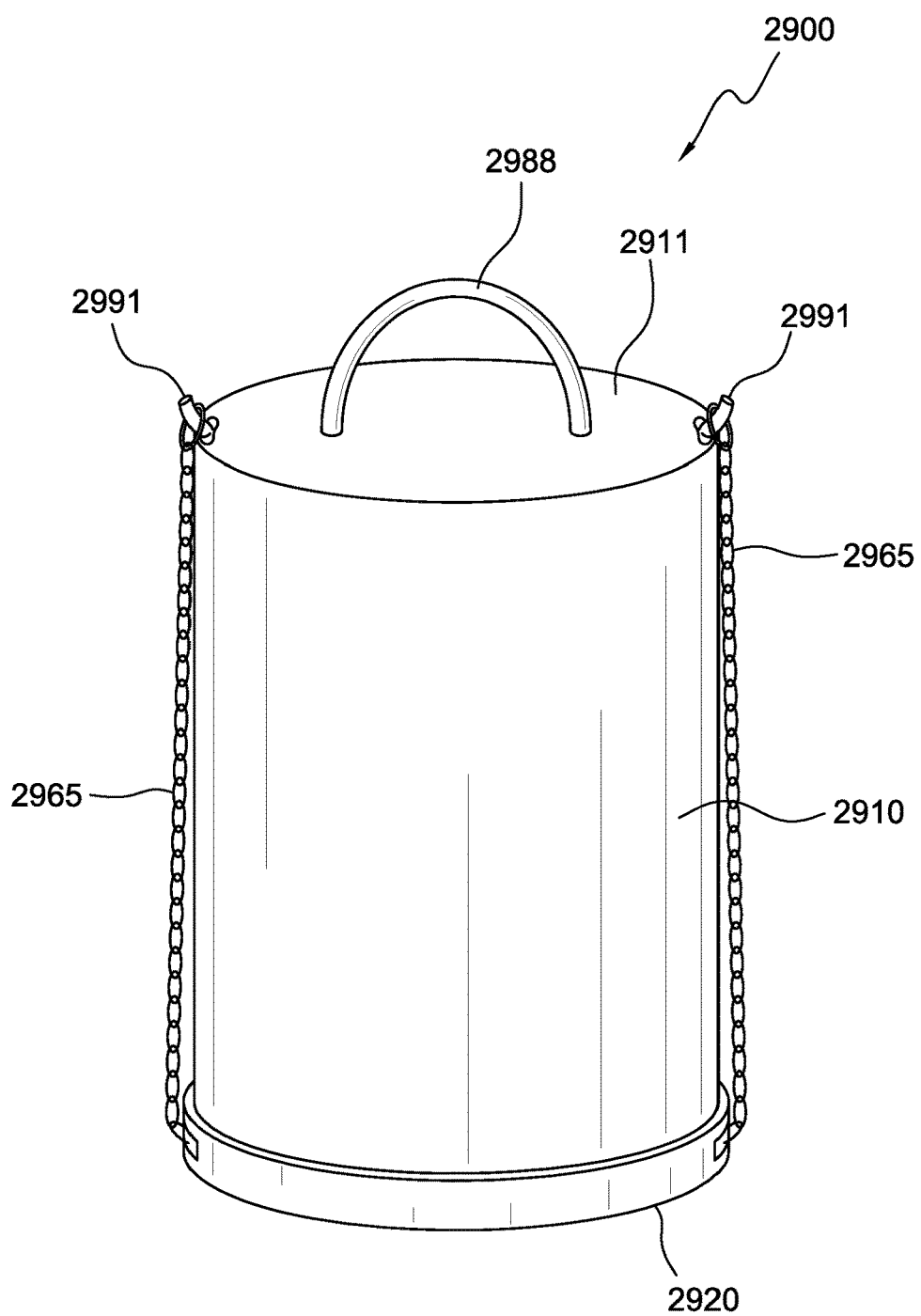
FIG. 30 shows a cylinder enclosure system in accordance with an embodiment.

In accordance with an embodiment, after a test cylinder is placed into cylinder enclosure system 2900, in the manner described herein, cover 2910 is placed onto base 2920, and chains 2965 are drawn up and attached to hooks 2991 on cover 2910, as shown in FIG. 30. The chains secure cover 2910 on base 2920. Once secured, cylinder enclosure system 2900 may be easily picked up by handles 2988 and transported from one location to a second location.

As discussed above, existing techniques for predicting the strength of a batch of concrete include use of standard test cylinders. Typically, specimens of concrete from a batch are poured into a plurality of test cylinders and allowed to dry. A technician may test the test cylinders at predetermined intervals (e.g., one cylinder every two days) to determine when the concrete has a desired strength. However, the strength measurements obtained in this manner are not always reliable. In particular, the humidity of the environment in which a batch of concrete dries affects the final strength of the concrete. Generally, greater humidity is associated with greater final strength. Because the final strength of a concrete mixture depends in part on the humidity of the environment in which the concrete dries, the final strength of a concrete mixture cannot be known without knowledge of the humidity of the environment in which the concrete dried. The humidity of the environment in which the concrete dried may not be known, for example, for various reasons including: if the test cylinders are maintained at an arbitrary location at a construction site, if the test cylinder is not sealed, if a test cylinder is inadvertently opened prior to the time designated for testing the cylinder, etc.

In accordance with an embodiment, a system including a sensing device and a smart cap system is used to generate a prediction of strength for a particular batch of concrete. The use of a smart cap system enables a user to obtain knowledge of the humidity profile of the environment in which a specimen of the concrete dries; the knowledge of the humidity profile is used to generate a prediction of the final strength of the batch of concrete with greater accuracy and reliability.

Figure 31:
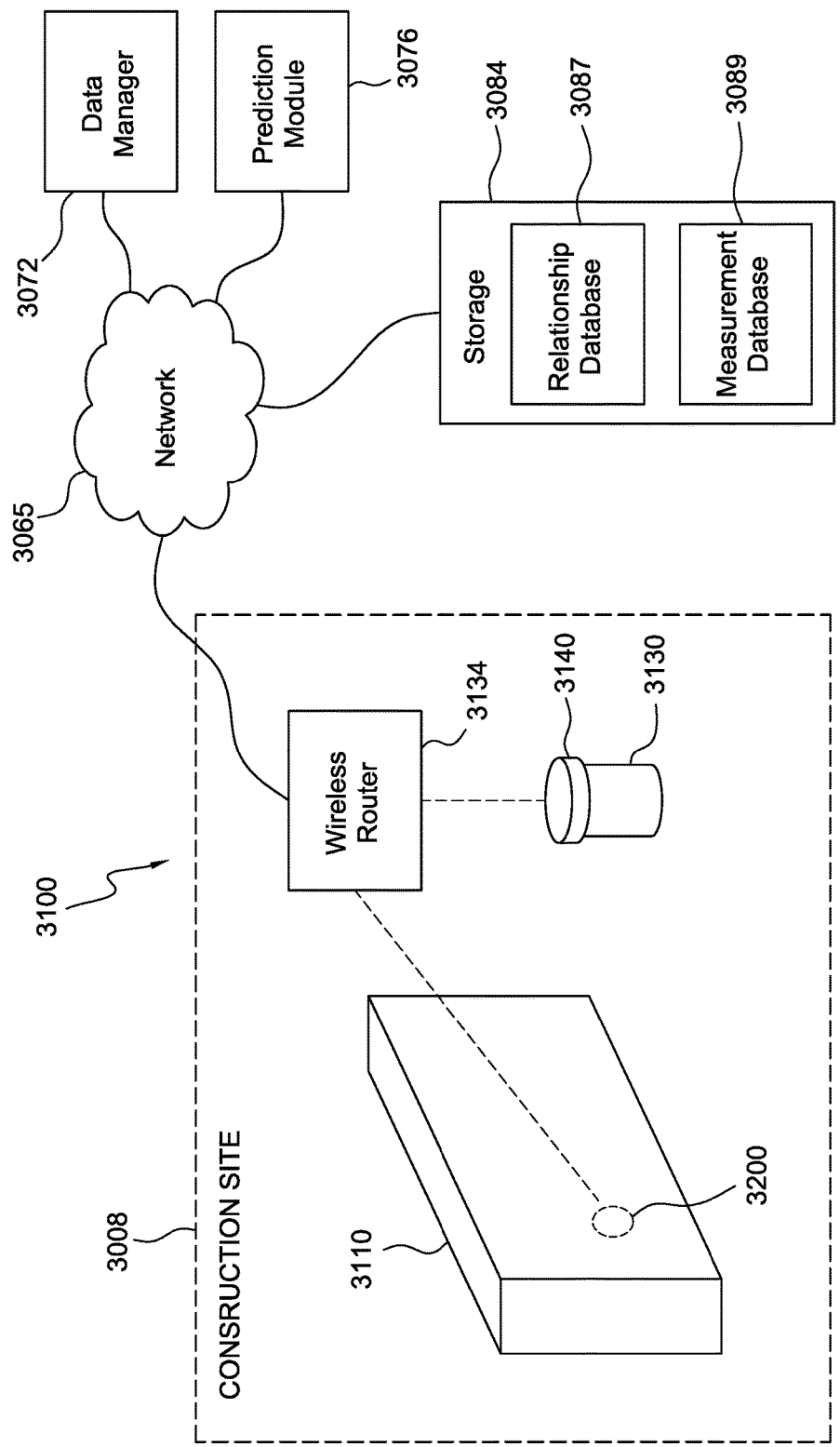
FIG. 31 shows a system in accordance with an embodiment.

FIG. 31 shows a system in accordance with an embodiment. System 3100 includes a sensing device 3200 that is embedded in a concrete structure and adapted to measure the temperature and humidity of the concrete, a cylinder 3130 holding a specimen of the concrete and a smart cap system 3140 fitted onto the cylinder, a wireless router 3134, a network 3065, a data manager 3072, a prediction module 3076, and a storage 3084. In the illustrative embodiment, sensing device 3200, cylinder 3130, smart cap system 3140, and wireless router 3134 are located at a construction site 3008. In other embodiments, components of system 3100 may be arranged differently. Wireless router 3134 is connected to network 3065, which may be the Internet, for example, or another type of network. Data manager 3072 and prediction module 3076 may include software residing and operating on one or more servers, for example, or may include hardware. Storage 3084 may include any type of storage or memory adapted to store data.

Sensing device 3200 is embedded in a structure 3110 formed from a concrete mixture. For example, sensing device 3200 may be placed into the concrete mixture while the concrete is still in a concrete mixing truck, or may be placed into the concrete mixture while the concrete is being poured into a form to create the structure, or at another time.

Sensing device 3200 obtains measurements of the temperature and humidity of the concrete mixture as it dries, and transmits the measurement data wirelessly to data manager 3072. For example, the data may be transmitted via wireless router 3134, and via network 3065 (which may include the Internet), to data manager 3072. The measurement data may be stored in memory 3084. For example, the measurement data may be stored in a measurement database 3089 maintained in storage 3084, shown in FIG. 31.

Figure 32A:
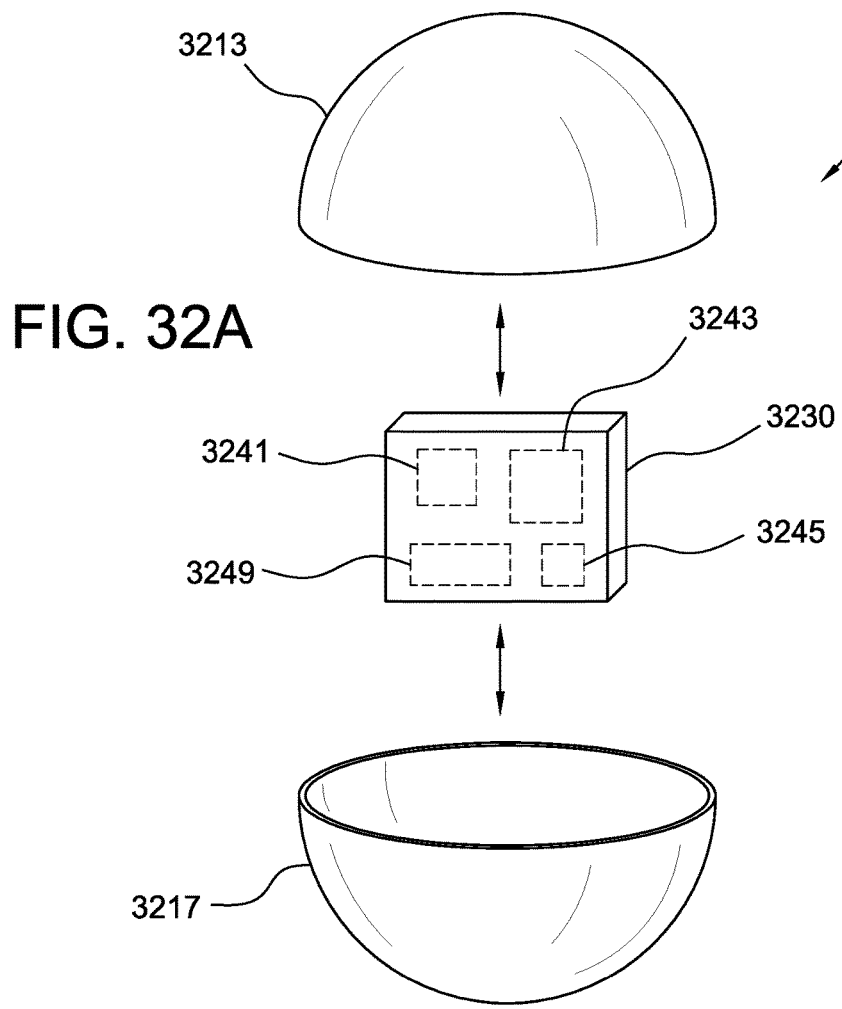
FIGS. 32A-32B show a sensing device in accordance with an embodiment.
Figure 32B:
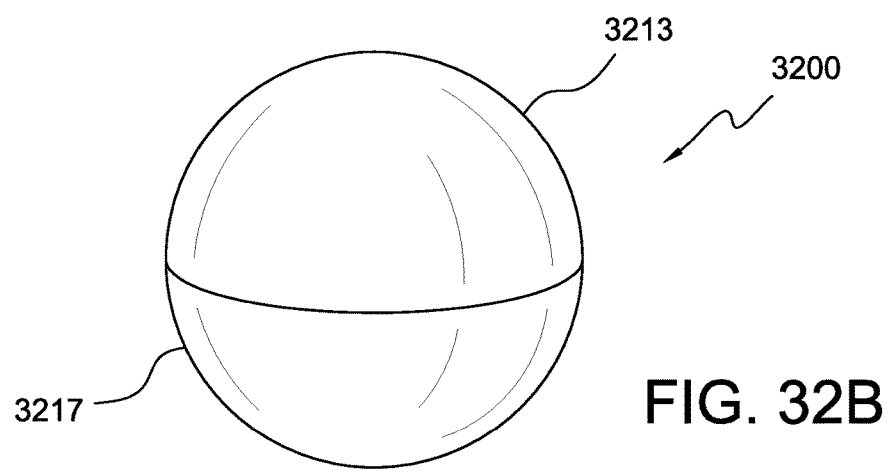

In the illustrative embodiment, sensing device 3200 is a spherical sensing device comprising one or more sensors. FIGS. 32A-32B show sensing device 3200 in accordance with an embodiment. FIG. 32A shows components of sensing device 3200. FIG. 32B shows sensing device 3200 in an assembled configuration.

Referring to FIG. 32A, sensing device 3200 includes a shell comprising a first portion 3213 and a second portion 3217. First and second portions 3213, 3217 are adapted to fit together to form an enclosed shell, as shown in FIG. 32B. First and second portions 3213, 3217 form a seal when fitted together which protects components located inside the device. While in the illustrative embodiment, sensing device 3200 is spherical, in other embodiments, a sensing device may have other shapes. Sensing device 3200 also includes a sensor device 3230 adapted to fit inside the shell when first and second portions 3213, 3217 are fitted together. Sensor device 3230 includes a plurality of sensors 3241, 3243, 3245, which include a temperature sensor and a humidity sensor, and may include other types of sensors adapted to measure other characteristics of a concrete mixture such as salinity, pH level, conductivity, impedance, etc. Sensor device 3230 also includes a transmitter 3249 adapted to transmit measurement data wirelessly.

In one embodiment, first and second portions 3213, 3217 are made of a suitable plastic material. In other embodiments, first and second portions 3213, 3217 may be formed from a different material such as rubber, metal, etc.

In accordance with an embodiment, first temperature and humidity measurements obtained by a sensing device embedded in a concrete structure, second temperature and humidity measurements obtained by a smart cap system located on a test cylinder containing a specimen of the concrete, and strength data obtained by testing the concrete in the test cylinder, are used to generate a prediction of the final strength of the concrete in the structure. One method of obtaining a prediction of final strength of a concrete mixture based on temperature, humidity, and strength measurements is described herein. However, other methods may be used to determine final strength from temperature, humidity and strength data. For example, any algorithm that derives the final strength of a concrete mixture based on temperature, humidity and strength measurements may be used.

Figure 33A:
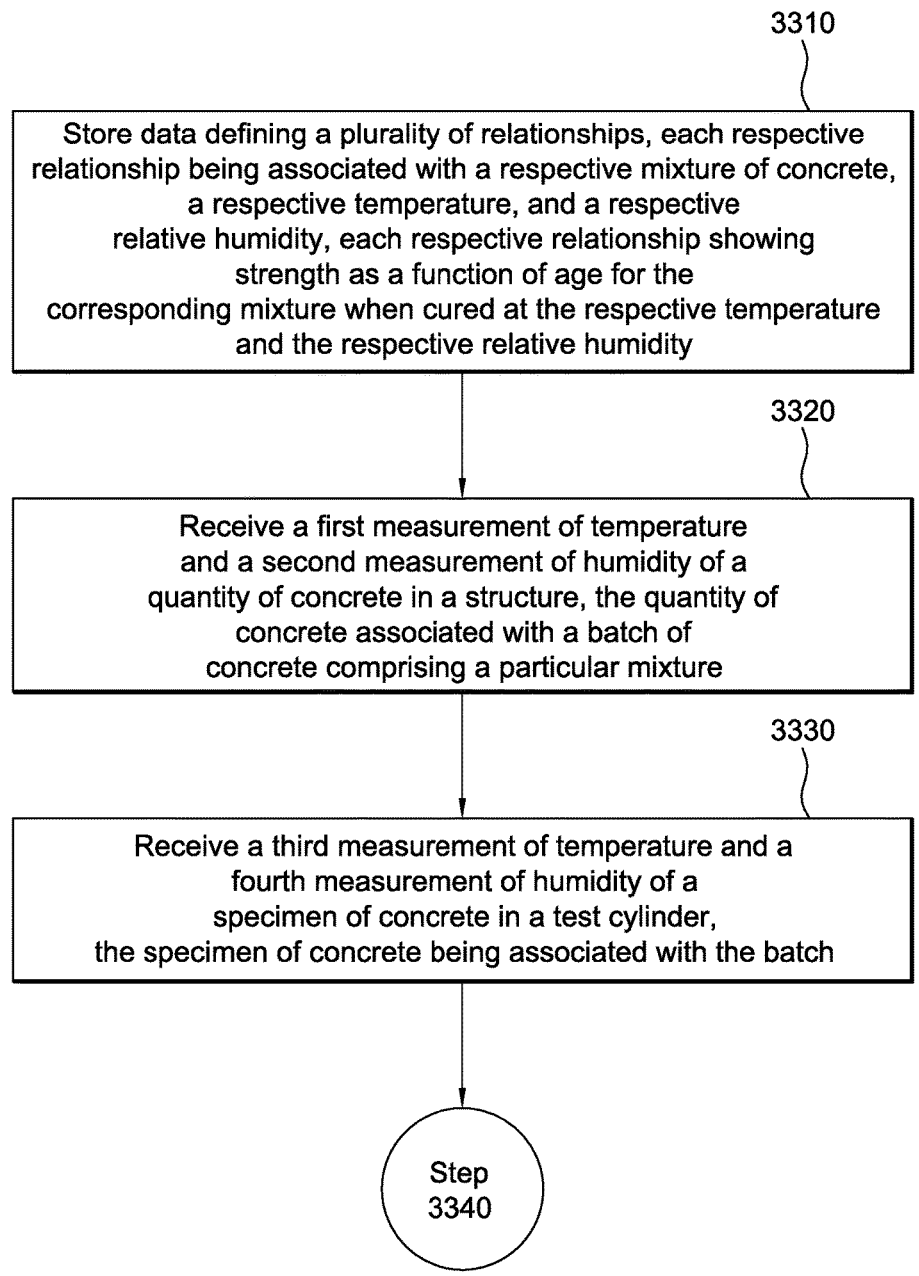
FIGS. 33A-33B include a flowchart of a method of generating a prediction of the strength of a batch of concrete in accordance with an embodiment.
Figure 33B:
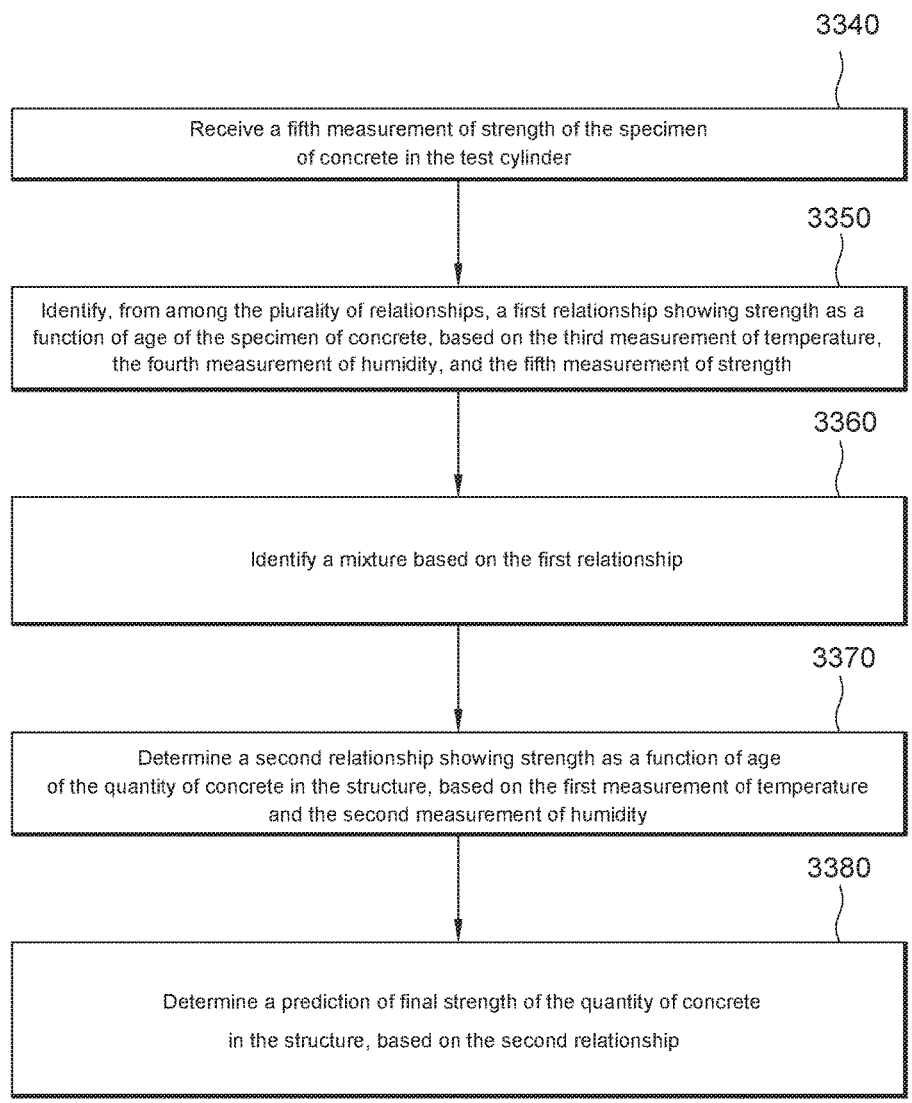
Figure 34:
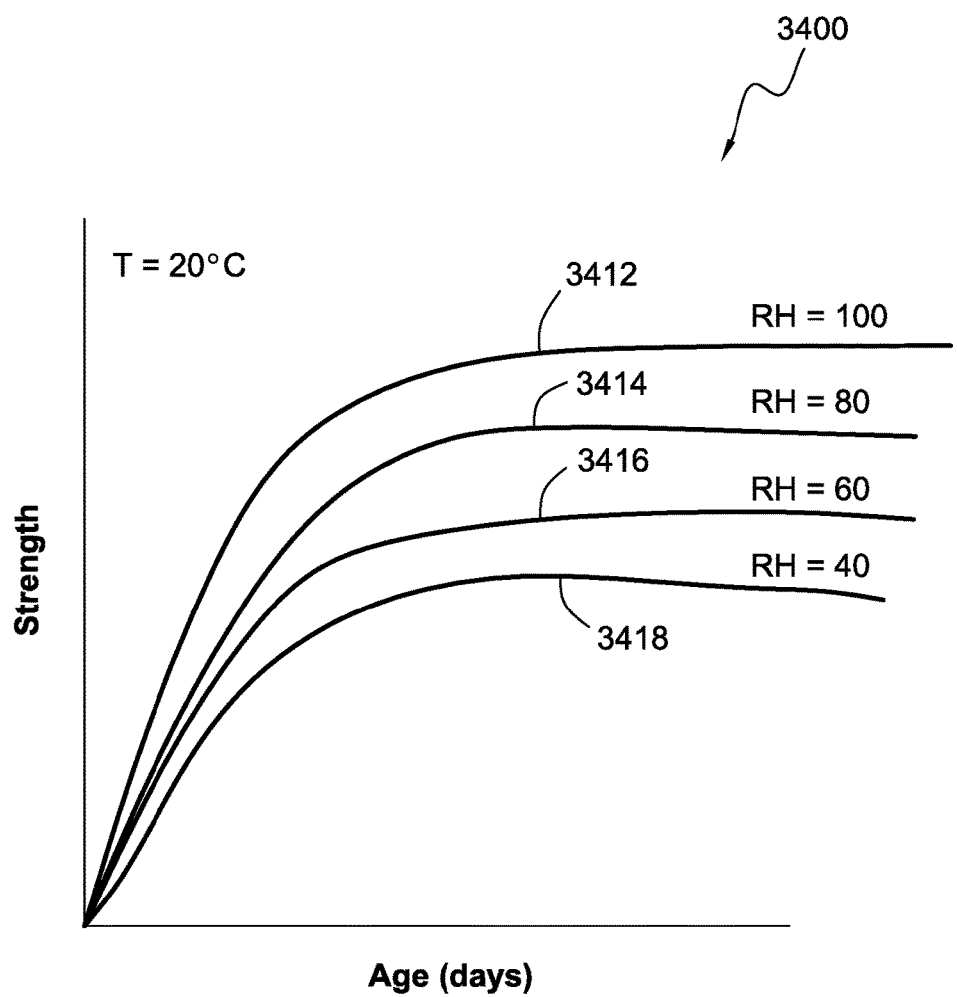
FIG. 34 shows a graph containing a set of relationships each showing strength as a function of age for a concrete mixture cured at a selected temperature in accordance with an embodiment.

FIGS. 33A-33B include a flowchart of a method of generating a prediction of the strength of a batch of concrete in accordance with an embodiment. At step 3310, data defining a plurality of relationships is stored, wherein each respective relationship is associated with a respective mixture of concrete, a respective temperature, and a respective relative humidity, and each respective relationship shows strength as a function of age for the corresponding mixture when cured at the respective temperature and the respective relative humidity. In one embodiment, a set of relationships such as that shown in FIG. 34 are generated a priori for each of a plurality of mixtures (under laboratory conditions). FIG. 34 shows a graph 3400 containing a set of curves (in this example, four curves) each showing strength as a function of age for a particular concrete mixture, when the concrete is cured at a selected temperature T (in this instance T=20° C.) in accordance with an embodiment. Each of the four relationships shown in graph 3400 show the relationship between strength and age for the mixture when the mixture is when cured in an environment having a selected relative humidity (RH). Thus, curve 3412 shows strength as a function of age when T=20° C. and RH=100; curve 3414 shows strength as a function of age when T=20° C. and RH=80; curve 3416 shows strength as a function of age when T=20° C. and RH=60; curve 3418 shows strength as a function of age when T=20° C. and RH=40.

In the illustrative embodiment, a plurality of relationships such as those shown in FIG. 34 (i.e., a plurality of curves such as curves 3412, 3414, 3416, 3418) are determined for each of a plurality of mixtures, temperatures, and relative humidities. As used herein, the term "mixture" signifies a particular combination of components such as water, cement, cementitious, fine aggregate, etc. A mixture may be a particular combination mixed precisely in accordance with a formulation, or may be a combination that is similar to a particular formulation but has been modified in some way. In practice, because a concrete mixture that is ordered based on a desired formulation is often modified by small additions of water, cement, and/or other components, the number of possible mixtures is very large. Thus, in the illustrative embodiment, a plurality of mixtures are defined, and for each mixture, a plurality of relationships showing strength as a function of curing age is determined for a plurality of selected temperatures and relative humidities.

Thus, for example, for a selected mixture, a first plurality of relationships may be determined for a curing temperature of 10° C. (e.g., a set of four curves for four different relative humidities may be determined), a second plurality of relationships may be determined for the curing temperature of 20° C., a second plurality of relationships may be determined for the curing temperature of 30° C., a second plurality of relationships may be determined for the curing temperature of 40° C., etc. Relationships may be determined for other curing temperatures.

The plurality of relationships are stored in a memory. In the illustrative embodiment of FIG. 31, the plurality of relationships are stored in a relationship database 3087 maintained in storage 3084, shown in FIG. 31.

In an illustrative example, a batch of concrete is now produced at a production facility and transported in a concrete mixing truck to a construction site. In the illustrative embodiment, the concrete is transported to construction site 3008 shown in FIG. 31. The concrete is poured to form structure 3110 at construction site 3008. For example, the structure may be a wall, a floor, etc.

At step 3320, a first measurement of temperature and a second measurement of humidity of a quantity of concrete in a structure, the quantity of concrete being associated with a batch of concrete comprising a particular mixture, are received. In the illustrative embodiment, sensing device 3200, while embedded in concrete structure 3110 (and while the concrete is drying), obtains one or more measurements of the temperature of the concrete and one or more measurements of the humidity of the concrete. Sensing device 3200 transmits data representing the temperature and humidity measurements wirelessly to data manager 3072. For example, the measurement data may be transmitted via wireless router 3134 and network 3065 to data manager 3072. Data manager 3072 receives the temperature measurement data and the humidity measurement data and stores the data in storage 3084.

In the illustrative embodiment, prediction module 3076 may access the temperature and humidity data generated by sensing device 3200 and generate a prediction of the concrete's maturity based on the temperature measurements received from the sensing device. However, the temperature and humidity measurements generated by sensing device 3200 are insufficient to generate a reliable prediction of the concrete's strength.

In the illustrative embodiment, a prediction of the final strength of the concrete in the structure is generated using the data generated by sensing device 3200 in combination with data obtained by smart cap system 3140. Specifically, at the time the concrete is poured to form structure 3110, a specimen of the concrete from the same batch is poured into test cylinder 3130, and smart cap system 3140 is placed on the cylinder. When smart cap system 3140 is placed on cylinder 3130, a seal is created in the manner described herein. Advantageously, the seal formed in this manner ensures that the concrete in cylinder 3130 dries in an environment having stable humidity. In one embodiment, smart cap system 3140 maintains the humidity within cylinder 3130 at or near one hundred percent (100%) throughout the curing process.

Also advantageously, smart cap system 3140 enables a user to obtain knowledge of the humidity of the environment in which the concrete in cylinder 3130 dries. Thus, while the concrete in the test cylinder 3130 is cured, sensors in smart cap system 3140 obtain measurements of the temperature and humidity of the concrete within the cylinder. As discussed above, the sealed smart cap system is able to provide an environment at or near one hundred percent humidity. The temperature and humidity measurement data are transmitted wirelessly to data manager 3072. For example, smart cap 3140 may transmit the measurement data via wireless router 3134 and network 3065 to data manager 3072.

At step 3330, a third measurement of temperature and a fourth measurement of humidity of a specimen of concrete in a test cylinder, the specimen of concrete being associated with the batch, are received. Data manager 3072 receives the temperature measurement data and humidity measurement data from smart cap system 3140. Data manager 3072 may store the measurement data in measurement database 3089 in storage 3084.

At a selected time, smart cap system 3140 is removed from cylinder 3130, the specimen of concrete is tested, and a measure of the strength of the specimen of the concrete is obtained. For example, well-known methods may be used to crush the concrete and to measure the strength of the concrete. The measurement of strength is transmitted to data manager 3072. For example, a technician who conducts the test may transmit the measurement data to data manager 3072 (e.g., by entering the strength data into a selected field on a web site, by entering the strength data via a cell phone App, by sending an email, etc.).

At step 3340, a fifth measurement of strength of the specimen of concrete in the test cylinder is received. Data manager 3072 receives the data representing the measurement of strength and stores the data in storage 3084.

The measure of strength obtained in this manner, and the temperature and humidity measurements previously obtained by sensing device 3200 and by smart cap system 3140, are now used to generate a prediction of the final strength of the batch of concrete.

It is to be noted that in the concrete production and construction fields, lack of knowledge of the exact composition of any particular batch of concrete is an ongoing problem. Because small additions and modifications are frequently made to any given concrete mixture at the production facility, during transport (in a concrete mixing truck), and at the construction site, the mixture that is poured at the construction site is often not the same as the mixture defined by the original formulation. This lack of certainty concerning the components of any given concrete mixture being poured adds to the challenge of predicting the strength of the mixture. Advantageously, the systems and methods described herein use temperature and humidity measurement data, and observed strength data, to determine the nature of the relevant concrete mixture. This knowledge is then used to identify a relationship between the strength and age of the mixture.

Referring again to the method of FIGS. 33A-33B, at step 3350, a first relationship showing strength as a function of age of the specimen of concrete is identified from among the plurality of relationships, based on the third measurement of temperature, the fourth measurement of humidity, and the fifth measurement of strength. In the illustrative embodiment, after smart cap system 3140 is removed from cylinder 3130, and the concrete in the cylinder is tested to determine its strength, the strength data, and the data indicating temperature and humidity, as well as age data, are used to identify, from among the stored relationships, a curve matching the strength, temperature, humidity, and age data. Specifically, a relationships stored in storage 3084 are examined and a relationship matching the temperature and humidity data obtained by smart cap 3140, the observed strength data, and the relevant age data, is identified.

At step 3360, a mixture is identified based on the first relationship. Because each of the stored relationships is associated with a particular mixture, after the curve is identified, the mixture that was used to produce the batch may be identified.

At step 3370, a second relationship showing strength as a function of age of the quantity of concrete in the structure is determined, based on the first measurement of temperature and the second measurement of humidity. In the illustrative embodiment, after the relevant mixture is identified, the temperature data obtained by the sensing device in the concrete of the structure is now used to determine the temperature profile experienced by the concrete as it cured. A plurality of curves representing strength profiles of the mixture at the curing temperature is retrieved from memory. For example, a set of curves (e.g., a graph with four curves) showing strength of the mixture as a function of age at the curing temperature (and at respective relative humidities) may be retrieved.

Now the humidity data obtained from sensing device 3200 in the structure is used to determine a relative humidity in which the concrete of the structure cured. After the relative humidity experienced by the concrete mixture of the structure is determined, a particular curve showing the strength profile of the mixture at the relevant temperature and humidity is identified. Thus, for example, a curve associated with the relevant relative humidity may be selected from among a set of curves on a graph. Alternatively, an intermediate curve may be extrapolated based on the curves defined in stored information.

At step 3380, a prediction of final strength for the concrete mixture of the structure is determined based on the identified curve. The relationship identified in step 3370 is used to determine a prediction of the final strength of the concrete mixture in structure 3110.

In one embodiment, a prediction of strength is provided to a user in the form of one or more probabilities. For example, a prediction may indicate a probability that a concrete mixture will have a desired strength (e.g., "There is a 90% chance that the strength of the concrete will be 3000 PSI.").

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:
1. A smart cap system comprising:
a cap adapted to fit on a concrete test cylinder, the cap comprising:
a top portion adapted to cover at least a portion of an opening of the concrete test cylinder, the top portion including a top interior surface;
a side portion adapted to fit around a circumference of the concrete test cylinder, the side portion including a side interior surface; and
a third interior surface disposed between the top interior surface and the side interior surface,
wherein:
the side interior surface and the third interior surface define an angle between twenty (20) and forty (40) degrees;
a greatest radius of the third interior surface is equal to or greater than a radius of the concrete test cylinder; and
the third interior surface includes a plurality of concentric ridges; and
a sensor holder system disposed on the top interior surface of the cap, the sensor holder system comprising:
a sensor enclosure component comprising:
a volume adapted to hold one or more sensors; and
a surface comprising one or more holes adapted to allow a flow of air to pass into the volume;
a cover component adapted to cover and protect the sensor enclosure component;
a fabric membrane disposed between the sensor enclosure component and the cover component, the fabric membrane being waterproof to prevent liquid from passing therethrough and breathable to enable water vapor to pass therethrough; and a humidity sensor disposed in the sensor enclosure component, the humidity sensor being adapted to obtain humidity measurements;

wherein no portion of the humidity sensor passes through the top interior surface, side interior surface, or third interior surface of the cap.

2. The smart cap system of claim 1, wherein the cap includes a double-walled structure having first and second walls and a volume between the first and second walls, wherein the volume holds one of air and a selected insulating material.

3. The smart cap system of claim 1, wherein the humidity sensor is adapted to obtain a measurement of a humidity of a concrete mixture disposed in the test cylinder.

4. The smart cap system of claim 3, wherein the cap is adapted to fit on one of a 4×8-inch cylinder, a 6×12-inch cylinder, a 150 mm cube, and a 200 mm cube.

5. The smart cap system of claim 3, further comprising one or more second sensors disposed in the sensor enclosure component, the one or more second sensors comprising one of a temperature sensor, a chronometer, a heat flow sensor, a motion sensor, a pH sensor, a location detector, a GPS sensor, an accelerometer, a triangulation sensor, a thermoelectric heat flow sensor, a salinity sensor, a macro fiber composite (MFC) sensor, and a capillary sensor.

6. The smart cap system of claim 3, further comprising:
a memory adapted to store data; and
a processor adapted to:
receive from the humidity sensor measurement data relating to the measurement of the humidity of the concrete mixture; and
generate a prediction of a second characteristic of the concrete mixture based on the measurement data.

* * * * *